United States Patent
Perrow

(10) Patent No.: US 9,113,852 B2
(45) Date of Patent: Aug. 25, 2015

(54) APPARATUS AND METHOD FOR ENLARGING AN INCISION

(71) Applicant: Pioneer Surgical Technology, Inc., Marquette, MI (US)

(72) Inventor: Scott J. Perrow, Ishpeming, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

(21) Appl. No.: 14/250,063

(22) Filed: Apr. 10, 2014

(65) Prior Publication Data

US 2014/0221760 A1  Aug. 7, 2014

Related U.S. Application Data

(63) Continuation of application No. 13/415,673, filed on Mar. 8, 2012, now Pat. No. 8,702,600.

(60) Provisional application No. 61/450,560, filed on Mar. 8, 2011.

(51) Int. Cl.
  *A61B 1/32* (2006.01)
  *A61B 17/02* (2006.01)
  (Continued)

(52) U.S. Cl.
  CPC . *A61B 17/02* (2013.01); *A61B 1/32* (2013.01); *A61B 17/025* (2013.01);
  (Continued)

(58) Field of Classification Search
  CPC ............... A61B 17/02; A61B 17/0293; A61B 17/0206; A61B 17/3421; A61B 17/3423; A61B 2017/3433; A61B 17/3439; A61B 17/0218

USPC .................................................. 600/184–246
  See application file for complete search history.

(56) References Cited

U.S. PATENT DOCUMENTS 2,473,266 A  6/1949  Wexler
2,623,517 A  12/1952  Barlow
(Continued)

FOREIGN PATENT DOCUMENTS

WO  03086202  10/2003
WO  2004047650  6/2004
(Continued)

OTHER PUBLICATIONS

Clarity Lateral, Retractor System, Surgical Technique, 2008, 12 pages.
(Continued)

*Primary Examiner* — Ellen C Hammond
*Assistant Examiner* — Christina Negrellirodrigue
(74) *Attorney, Agent, or Firm* — Fitch, Even, Tabin & Flannery LLP

(57) ABSTRACT

A retraction system and method are provided for retracting tissues surrounding a surgical site. In one aspect, a method including engaging slide connections between a guide dilator and a plurality of tissue engaging members and sequentially enlarging an incision using the guide dilator and the plurality of tissue engaging members. In another aspect, a method of inserting a plurality of tissue engaging members into an incision including fixing tip portions of the plurality of tissue engaging members in an insertion configuration, advancing the tip portions into an incision, and restricting movement of the tip portions away from the insertion configuration. A guide dilator system comprising an elongate body, a plurality of tissue engaging members, and slide connections between the elongate body and the tissue engaging members is also provided.

23 Claims, 44 Drawing Sheets

(51) Int. Cl.
*A61B 19/00* (2006.01)
*A61B 17/00* (2006.01)

(52) U.S. Cl.
CPC ........ *A61B 17/0206* (2013.01); *A61B 19/5202* (2013.01); *A61B 2017/00261* (2013.01); *A61B 2017/0256* (2013.01); *A61B 2017/0262* (2013.01)

(56) References Cited

U.S. PATENT DOCUMENTS

| | | | |
|---|---|---|---|
| 3,038,468 A | 6/1962 | Raeuchle | |
| 3,724,449 A | 4/1973 | Gauthier | |
| 3,948,259 A | 4/1976 | Bolduc et al. | |
| 3,998,217 A | 12/1976 | Trumbull et al. | |
| 4,010,741 A | 3/1977 | Gauthier | |
| 4,434,791 A | 3/1984 | Darnell | |
| 5,667,481 A | 9/1997 | Villalta | |
| 5,688,223 A | 11/1997 | Rosendahl | |
| 5,728,046 A | 3/1998 | Mayer | |
| 5,813,978 A | 9/1998 | Jako | |
| 5,928,139 A | 7/1999 | Koros | |
| 5,944,658 A | 8/1999 | Koros | |
| 5,954,635 A | 9/1999 | Foley | |
| 5,957,927 A | 9/1999 | Magee | |
| 5,967,973 A | 10/1999 | Sherts | |
| 6,083,154 A | 7/2000 | Liu | |
| 6,139,493 A | 10/2000 | Koros | |
| 6,206,826 B1 | 3/2001 | Mathews | |
| 6,213,940 B1 | 4/2001 | Sherts | |
| 6,224,545 B1 | 5/2001 | Cocchia | |
| 6,322,500 B1 | 11/2001 | Sikora | |
| 6,416,467 B1 | 7/2002 | McMillin | |
| 6,464,634 B1 | 10/2002 | Fraser | |
| 6,616,605 B2 | 9/2003 | Wright | |
| 6,800,084 B2 | 10/2004 | Davison | |
| 6,849,064 B2 | 2/2005 | Hamada | |
| 6,869,398 B2 | 3/2005 | Obenchain | |
| 6,896,654 B2 | 5/2005 | Paolitto | |
| 6,932,764 B2 | 8/2005 | Kashyap | |
| 7,195,592 B2 | 3/2007 | Ravikumar | |
| 7,780,594 B2 | 8/2010 | Hutton | |
| 7,985,179 B2 | 7/2011 | Gephart | |
| 8,702,600 B2 | 4/2014 | Perrow | |
| 2002/0111538 A1 | 8/2002 | Wright | |
| 2002/0193666 A1 | 12/2002 | Sherts | |
| 2003/0191371 A1 | 10/2003 | Smith | |
| 2004/0002629 A1 | 1/2004 | Branch | |
| 2004/0059193 A1 | 3/2004 | Fanous | |
| 2004/0087833 A1 | 5/2004 | Bauer | |
| 2004/0133077 A1 | 7/2004 | Obenchain | |
| 2004/0133201 A1 | 7/2004 | Shluzas | |
| 2004/0176665 A1 | 9/2004 | Branch | |
| 2004/0193018 A1 | 9/2004 | Thalgott | |
| 2004/0230100 A1 | 11/2004 | Shluzas | |
| 2004/0242969 A1 | 12/2004 | Sherts | |
| 2005/0080320 A1 | 4/2005 | Lee | |
| 2005/0137461 A1 | 6/2005 | Marchek | |
| 2005/0149035 A1 | 7/2005 | Pimenta | |
| 2005/0159650 A1 | 7/2005 | Raymond | |
| 2005/0159651 A1 | 7/2005 | Raymond | |
| 2005/0192485 A1 | 9/2005 | Branch | |
| 2005/0215862 A1 | 9/2005 | Larson | |
| 2005/0215866 A1 | 9/2005 | Kim | |
| 2005/0234304 A1 | 10/2005 | Dewey | |
| 2005/0261694 A1 | 11/2005 | Orton | |
| 2005/0277812 A1 | 12/2005 | Myles | |
| 2006/0004261 A1 | 1/2006 | Douglas | |
| 2006/0030858 A1 | 2/2006 | Simonson | |
| 2006/0052672 A1 | 3/2006 | Landry | |
| 2006/0074445 A1 | 4/2006 | Gerber | |
| 2006/0224044 A1 | 10/2006 | Marchek | |
| 2007/0118022 A1 | 5/2007 | Hutton | |
| 2007/0156025 A1 | 7/2007 | Marchek | |
| 2007/0161867 A1 | 7/2007 | Fowler | |
| 2007/0203399 A1 | 8/2007 | Gephart | |
| 2007/0238932 A1 | 10/2007 | Jones | |
| 2007/0282171 A1 | 12/2007 | Karpowicz | |
| 2008/0033251 A1* | 2/2008 | Araghi | 600/235 |
| 2008/0188718 A1* | 8/2008 | Spitler et al. | 600/213 |
| 2008/0214898 A1 | 9/2008 | Warren | |
| 2009/0069635 A1 | 3/2009 | Gephart | |

FOREIGN PATENT DOCUMENTS

| | | |
|---|---|---|
| WO | 2005092206 | 6/2005 |
| WO | 2005094695 | 10/2005 |
| WO | 2005096735 | 10/2005 |
| WO | 2007087536 | 8/2007 |

OTHER PUBLICATIONS

ProAccess Radiolucent Retractor Blades, SYTHES Spine, product offerings guide provided by the manufacturer, 2004, 2 pages, Paoli, Pennsylvania.

SynFrame Access and Retractor System Assembly Guide, SYNTHES Spine, assembly guide provided by the manufacturer, 1999, 12 pages, Paoli, Pennsylvania.

Webb, J., Spine-the future, AO foundation Webpage, available at: http://www.aofoundationorg/ AOFileServer/PortaiFiles?FilesPath=/Extranet2007/active/_attlwor/act!Dialogue/1999_2/spine.pdf, accessed Apr. 10, 2009.

* cited by examiner

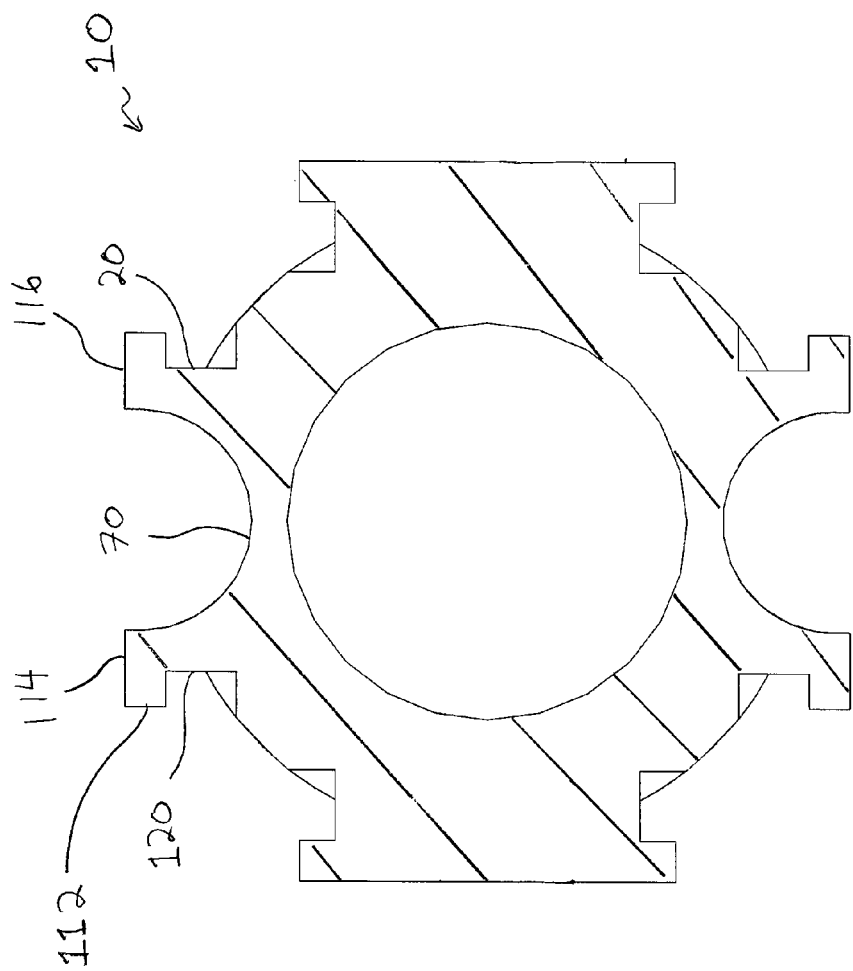

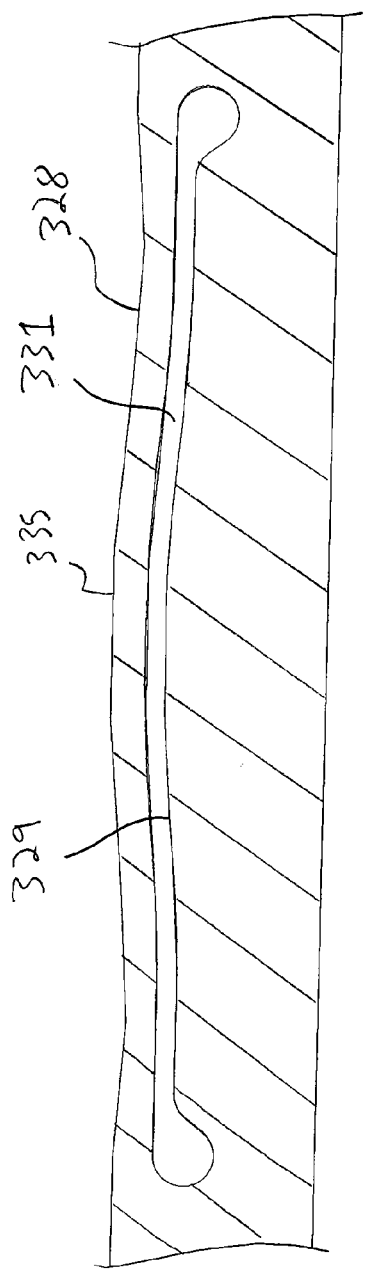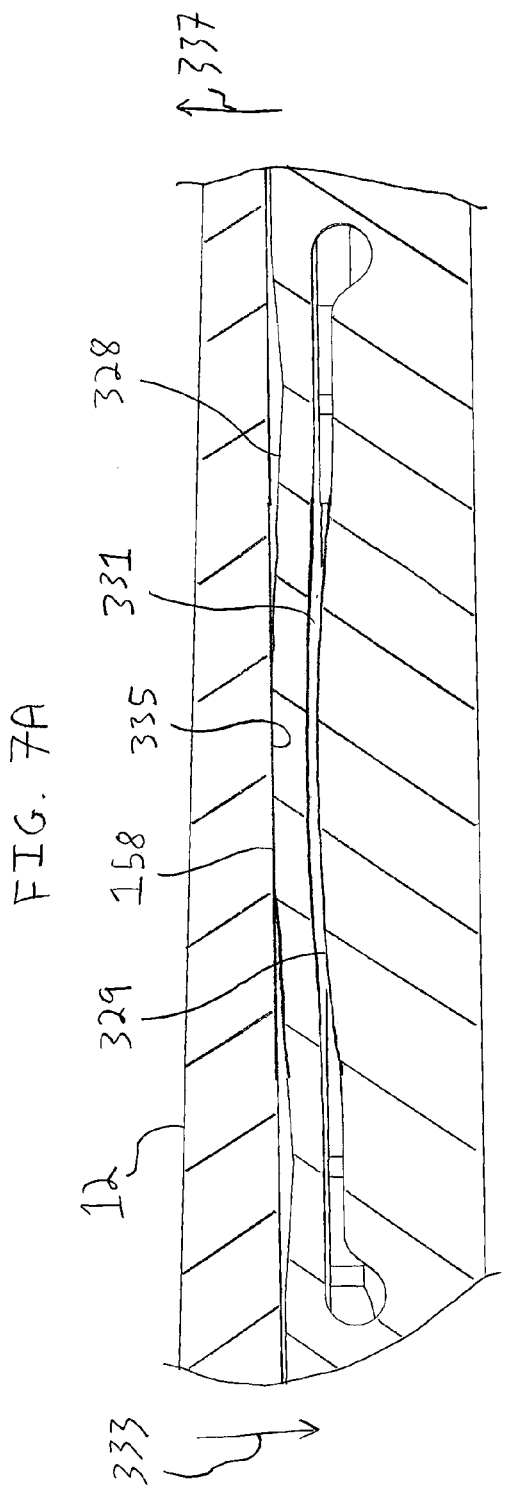
FIG. 7A
FIG. 7B

APPARATUS AND METHOD FOR ENLARGING AN INCISION

CROSS-REFERENCE TO RELATED APPLICATION

This application is a continuation of U.S. patent application Ser. No. 13/415,673, filed Mar. 8, 2012, which claims the benefit of U.S. Provisional Patent Application No. 61/450,560, filed Mar. 8, 2011, both of which are hereby incorporated by reference in their entireties.

FIELD OF THE INVENTION

The invention relates to a system and method for providing access to a surgical site and, more particularly, to a system and method for retracting tissue during a surgical procedure.

BACKGROUND OF THE INVENTION

Advancing blades of a surgical retractor through an incision and into position adjacent a surgical site involves overcoming resistance from muscles, tendons, and other tissues within the body. When the surgical retractor is used to access a patient's spine from the side of the patient, known as lateral approach surgery, the distance to the patient's spine is greater than if the spine were accessed through the patient's back, known as posterior approach surgery. The increased distance to the spine during lateral approach surgery means overcoming a greater amount of resistance from muscles, tendons, and other tissues in order to advance the retractor blades to the surgical site than in a posterior approach surgery.

Another difficulty with lateral approach surgery is that the tissues surrounding the retractor blades tightly envelop and deflect the blades as the blades are slid along a dilator toward the surgical site. The increased distance to the spine for lateral approach surgery means that the retractor blades must be longer in order to retract tissues adjacent the surgical site. Like cantilever beams, the longer retractor blades used for lateral approach surgery are subjected to forces from the surrounding tissues that deflect the blades a greater amount than if the blades were shorter blades typically used for posterior approach surgery. Deflection of the long retractor blades allows the tissues enveloping the blades to lodge between the blades and the dilator as well as creep into gaps between the blades. The retractor blades may have to be removed and re-inserted into the patient to remove tissues caught between the blades and the dilator or caught in gaps between the blades, which complicates the surgical procedure.

For longer length blades, such as the 80 mm-180 mm blades typically used for lateral approach surgery, small manufacturing variations in straightness along the blades are magnified by the length of the blades. These variations are problematic, as even a slight curvature may cause the tip of a longer blade to lift up from the dilator and trap tissue as the blade is advanced toward the surgical site. Variations in blade straightness may also cause the tips of the retractor blades to be unevenly spaced around the dilator and permit tissue creep between the retractor blades. These situations increase the difficulty of advancing the retractor blades toward the surgical site and complicate the process of establishing a working channel to the spine.

SUMMARY OF THE INVENTION

In one aspect of the invention, a method is provided for enlarging an incision that limits tissue creep as tissue engaging members are advanced into an incision and substantially improves the ease with which a surgeon may establish a working channel within a patient. More specifically, the method involves engaging slide connections between a plurality of tissue engaging members and a guide dilator which restricts separation of the tissue engaging members and accompanying tissue creep therebetween. Engaging slide connections between the tissue engaging members and the guide dilator also limits tissues lodging between the tissue engaging members and the guide dilator by resisting separation of the tissue engaging members from the guide dilator. Further, the method involves advancing a leading end portion of the guide dilator into the incision to enlarge the incision to an initial opening and advancing distal end portions of the tissue engaging members connected to the guide dilator into the incision to enlarge the initial opening to a larger, intermediate-sized opening. In this manner, the leading end portion of the guide dilator and the distal end portions of the tissue engaging members sequentially dilate the incision and minimize strain on tissues surrounding the incision. In one approach, the method further comprises withdrawing the leading end portion of the guide dilator from the incision while restricting movement of the plurality of the tissue engaging members. This disengages the slide connections between the plurality of tissue engaging members and the guide dilator without having to individually disconnect the tissue engaging members or utilize another tool to disconnect the tissue engaging members from the guide dilator. Accordingly, the present method provides an easier and faster approach for advancing tissue engaging members into position adjacent a surgical site while limiting interference from bodily tissues.

In another aspect of the invention, a method is provided for inserting tissue engaging members into an incision that limits tissue creep even if the tissue engaging members are longer and have varying degrees of straightness. The method includes fixing tip portions of the tissue engaging members in a predetermined insertion configuration and advancing the tip portions into an incision. This way, any variation in the straightness of one or more of the tissue engaging members is compensated for by manipulating the associated tip portion(s) into the predetermined insertion configuration before the tip portions are advanced into the incision. The method further comprises restricting movement of the tip portions of the tissue engaging members away from the insertion configuration. In this manner, the tip portions may be held in the insertion configuration against resistance from bodily tissues as the tip portions are advanced within the patient. In one approach, fixing the tip portions of the plurality of tissue engaging members comprises engaging slide connections between the tissue engaging members and a guide dilator. The slide connections permit a surgeon to rapidly connect the tissue engaging members to the guide dilator and insert the guide dilator and tissue engaging members into the incision without muscle, tendons, or other tissues shifting the tip portions of the tissue engaging members from the predetermined insertion configuration.

A guide dilator system is also provided including an elongate body, a plurality of tissue engaging members, and slide connections between the elongate body and the plurality of tissue engaging members. In this manner, the tissue engaging members can be easily engaged with the elongate body, advanced into an incision, and disengaged from the elongate body adjacent a surgical site. In one form, the slide connections comprise axially extending surfaces of each slide connection that extend a majority of a predetermined length of the respective tissue engaging members with the tissue engaging members in an operative position. In this manner, the slide connections provide a firm engagement between the tissue engaging members and the elongate body when the tissue engaging members are in an operative position on and connected to the elongate body.

The elongate body and the tissue engaging members may further include stop portions configured to abut and limit sliding of the tissue engaging members along the elongate body in a predetermined direction. For example, the predetermined direction can be from a leading end portion of the elongate body toward a trailing end portion of the elongate body. As the leading end portion of the elongate body is advanced toward the surgical site, the stop portions of the elongate body and the tissue engaging members abut and keep the tissue engaging members from sliding off of the elongate body as the surrounding tissues resist movement of the elongate body and the tissue engaging members within the patient. Once the tissue engaging members are positioned adjacent a surgical site, the elongate body is withdrawn from the incision which slides the tissue engaging members off of the elongate body. In this manner, the guide dilator system can simplify and accelerate the process of advancing the tissue engaging members into position adjacent a surgical site.

BRIEF DESCRIPTION OF THE DRAWINGS

FIG. 3A is a cross sectional view of the guide dilator taken across line 3A-3A in FIG. 3 showing flanges of the mounting rails which engage cooperating slots on the retractor blades;

FIG. 7A is a cross sectional view taken across line 7A-7A in FIG. 7 showing a resilient member of one of the mounting rails of the guide dilator of FIG. 7;

FIG. 7B is a cross sectional view similar to FIG. 7A showing the resilient member deflected downward and engaged with a retractor blade connected to the mounting rail;

DETAILED DESCRIPTION OF THE PREFERRED EMBODIMENTS

In FIGS. 1-6, a guide dilator 10 for inserting tissue engaging members, such as retractor blades 12, 14, 16, 18, through an incision and into position adjacent a surgical site is provided. The guide dilator 10 provides a rigid support for the retractor blades 12, 14, 16, 18 as the guide dilator 10, and the retractor blades 12, 14, 16, 18 connected thereto, slide along one or more initial dilators 516, 520 (see FIG. 12) into position adjacent a surgical site. The guide dilator 10 supports the retractor blades 12, 14, 16, 18 against resistance from muscles, tendons, and other tissues and to limit splaying of the retractor blades 12, 14, 16, 18 as they are advanced along the guide dilator 10 into the incision. In this manner, the guide dilator 10 allows a surgeon to easily advance the retractor blades 12, 14, 16, 18 into an incision without the retractor blades 12, 14, 16, 18 shifting and permitting tissues to encroach into gaps between the blades 12, 14, 16, 18.

Figure 1:
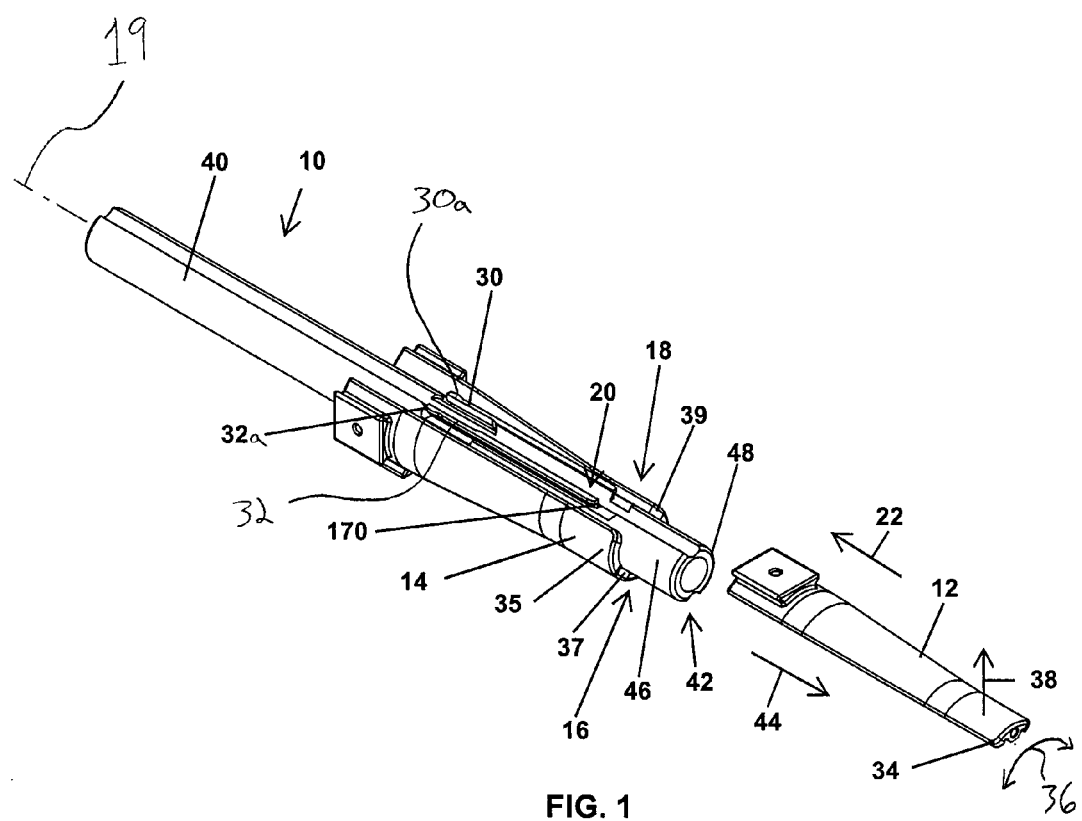
FIG. 1 is a perspective view of a guide dilator and retractor blades in accordance with one form of the present invention showing one of the retractor blades slid off of the guide dilator.

With reference to FIG. 1, the guide dilator 10 has a generally tubular configuration extending along a longitudinal axis 19. Further, the guide dilator 10 has slide connections with the retractor blades 12, 14, 16, 18, such as a mounting rail 20 that is received in sliding engagement in a slot 190 (see FIG. 5) on the blade 12, which permit the blades 12, 14, 16, 18 to be easily slid onto the guide dilator 10 in direction 22 and off of the guide dilator 10 in direction 44, as shown in FIG. 1. This way, the guide dilator 10 and blades 12, 14, 16, 18 can be rapidly and securely assembled during a surgery. The slide connections have stop portions, such as a lower end wall 170 of the mounting rail 20 and a stop surface 174 (see FIG. 5) of the blade 12, which are configured to abut and keep the blades 12, 14, 16, 18 from sliding off of the guide dilator 10 in direction 22 as tissues resist movement of the blades 12, 14, 16, 18 into an incision.

Figure 5:
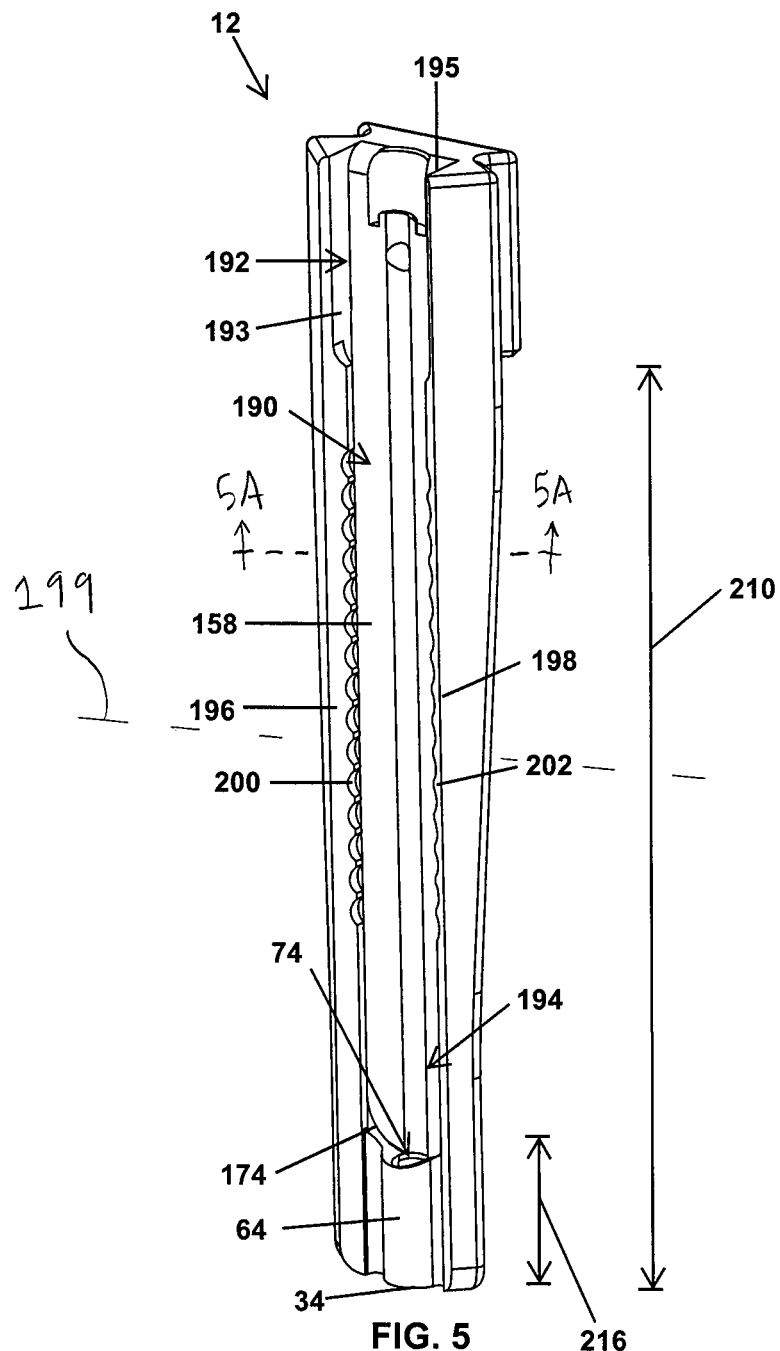
FIG. 5 is a perspective view of one of the retractor blades of FIG. 1 showing a slot of the blade for slideably receiving a mounting rail of the guide dilator and a cannula disposed at the distal end of the retractor blade.

In one form, the guide dilator 10 has a tissue engaging member retention mechanism, such as resilient arms 30, 32 of the mounting rail 20 which have distal ends 30a, 30b configured to be spaced apart by a distance that is greater than a width of the slot 190 of retractor blade 12 (see FIG. 5). When the blade 12 is slid onto mounting rail 20, the blade 12 deflects the distal ends 30a, 30b of the arms 30, 32 toward each other. The deflected arms 30, 32 resiliently bias against and frictionally engage surfaces 193, 195 of the slot 190. In this manner the tissue engaging member retention mechanisms engage the blades 12, 14, 16, 18 and provide resistance to removal of the blades 12, 14, 16, 18 from the guide dilator 10, as shown in FIG. 1. The frictional resistance is sufficient to keep the blades 12, 14, 16, 18 engaged with the guide dilator 10 when the guide dilator 10 is assembled and handled within the operating room, but permit the blades 12, 14, 16, 18 to be slid off of the guide dilator 10 when the blades 12, 14, 16, 18 are at a desired position within a patient. In this manner, the guide dilator 10 provides an elegant solution to the problem of handling the retractor blades 12, 14, 16, 18 throughout a surgical procedure.

A trailing end portion 40 of the guide dilator 10 is grasped after the retractor blades 12, 14, 16, 18 are mounted on the guide dilator 10 and a leading end portion 42 of the guide dilator 10 is advanced into an incision in direction 44, as shown in FIG. 1. Once the leading end portion 42 reaches the surgical site through the incision, the blades 12, 14, 16, 18 are slid downward in direction 44 along an outer bearing surface 46 of the leading end portion 42 until distal ends of the retractor blades 12, 14, 16, 18 reach an end 48 of the guide dilator 10. Next, a surgical retractor is connected to the blades 12, 14, 16, 18 to hold the retractor blades stationary in the incision and the guide dilator 10 is withdrawn from the incision in direction 22. The relative movement between the guide dilator 10 and the retractor blades 12, 14, 16, 18 withdraws guide dilator mounting rails 20, 92, 94, 96 (see FIG. 3) from associated slots in the blades 12, 14, 16, 18 and disengages the guide dilator 10 from the blades 12, 14, 16, 18. In this manner, moving the guide dilator 10 in a linear motion in direction 44 into an incision advances the connected retractor blades 12, 14, 16, 18 to a desired position adjacent a surgical site, and a reverse, linear motion in direction 22 disengages the guide dilator 10 from the blades 12, 14, 16, 18 and withdraws the guide dilator 10 from the incision in a single linear motion. As is apparent, this is an intuitive and speedy procedure for inserting retractor blades into position adjacent a surgical site.

With reference to the blade 12 in FIG. 1, the connection between the retractor blade 12 and the mounting rail 20 holds a tip 34 of the blade 12 against sliding in rotary direction 36 around the guide dilator 10 and radially away from the guide dilator 10 in direction 38. The connections between the mounting rails 92, 94, 96 and the blades 14, 16, 18 similarly limit movement of tips 35, 37, 39 of the blades 14, 16, 18 around and radially away from the guide dilator 10. In contrast to some previous techniques, where tissues could shift retractor blades as the blades were slid along a dilator into an incision, the guide dilator 10 holds retractor blade tips 34, 35, 37, 39 in a predetermined orientation around the guide dilator 10 against deflection and tissue creep until the guide dilator 10 is disengaged from the retractor blades 12, 14, 16, 18.

Figure 2:
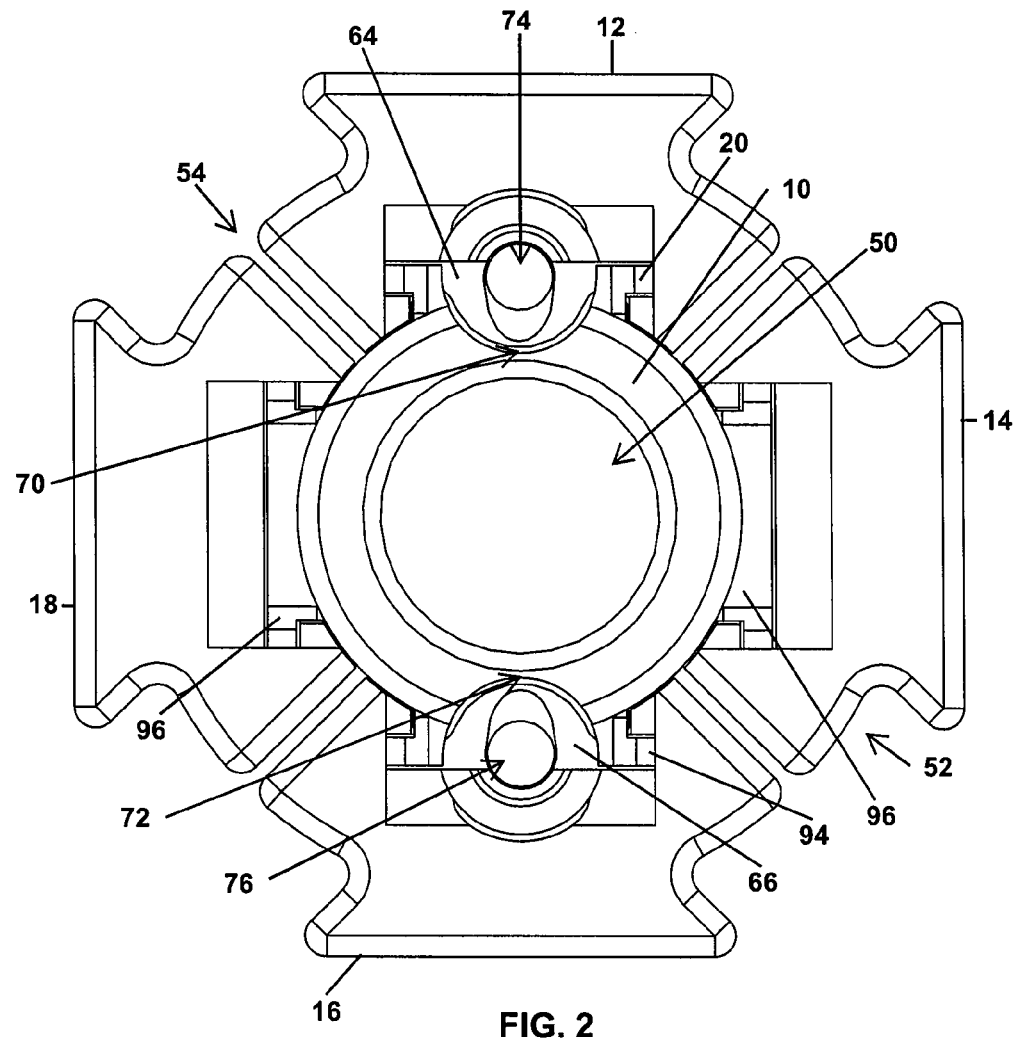
FIG. 2 is an enlarged, end view of the guide dilator of FIG. 1 with all of the retractor blades connected to the guide dilator showing an outer profile of the retractor blades.

Turning to FIG. 2, the guide dilator 10 has a central cannula 50 that permits the guide dilator 10 and connected retractor blades 12, 14, 16, 18 to be slid over one or more dilators used to initially enlarge an incision, as will be discussed in greater detail below. The blades 12, 14, 16, 18 form a round outer profile 52 around the guide dilator 10 interrupted by gap spacings 54 between adjacent retractor blades. With the blades 12, 14, 16, 18 connected to guide dilator 10 and the blade distal ends 34, 35, 37, 39 spaced from the guide dilator end 48, as shown in FIG. 1, the generally cylindrical leading end portion 42 of the guide dilator 10 and the round outer profile 52 of the blade distal ends 34, 35, 37, 39 sequentially dilate an incision and minimize stresses on the tissues surrounding the incision. In an alternative embodiment, the guide dilator 10 may lack a central cannula 50 and instead have a generally cylindrical configuration. In this approach, the leading end portion 42 may have a configuration to provide a controlled dilation of the incision.

Figure 3:
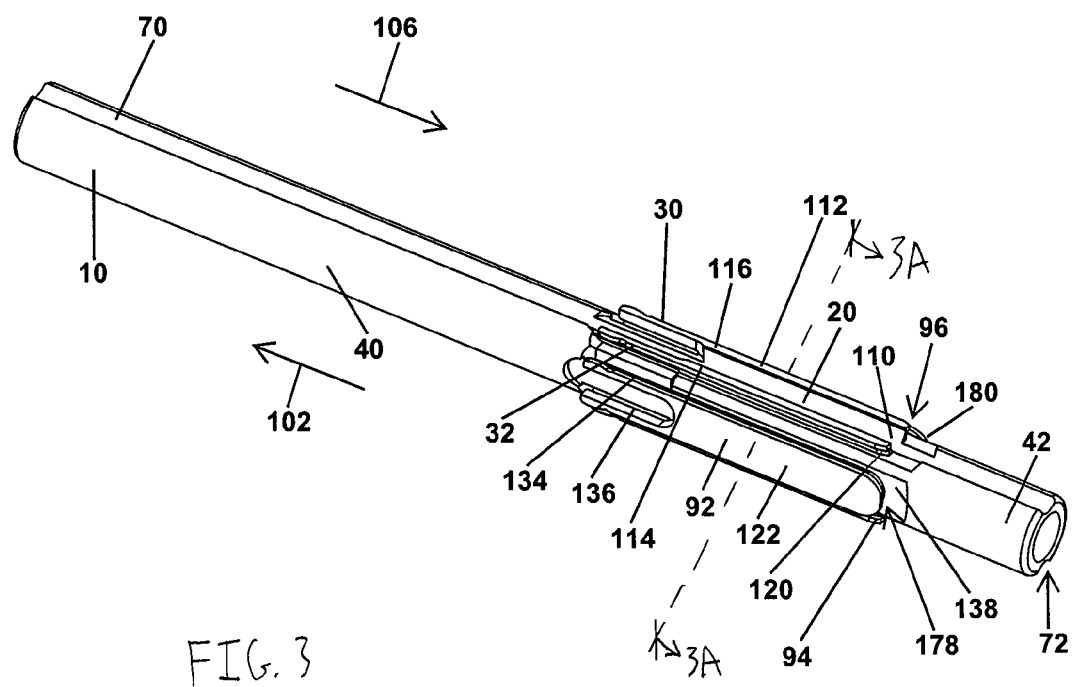
FIG. 3 is a perspective view of the guide dilator of FIG. 1 showing mounting rails of the guide dilator for slideably engaging in slots of the retractor blades of FIG. 1.

The guide dilator 10 and connected retractor blades 12, 14, 16, and 18 provide additional functionality once the guide dilator 10 reaches the surgical site. For example, the retractor blades 12, 16 are cannulated blades having cylindrical portions 64, 66 extending radially inward into grooves 70, 72 which extend along the length of the guide dilator 10, as shown in FIGS. 2, 3, and 5. The cylindrical portions 64, 66 have throughbores or cannulas 74, 76 that are unobstructed even when the blades 12, 16 are connected to the mounting rails 20, 94. A fixation pin, nerve monitoring probe, or other tool may be inserted along the grooves 70, 72 and into either one of the cannulas 74, 76 once the guide dilator and retractor blades 12 have been advanced to the surgical site. The presence of the unobstructed cannulas 74, 76 also provides a visual window for a surgeon to observe the tissues and bones directly beneath the blades 12, 16 without having to remove the retractor blades 12, 16 from the guide dilator 10. In one approach, a surgeon can visually check whether one of the cannulas 74, 76 is above a vertebra by looking through the cannula 74, 76 before driving a fixation pin through the cannula 74, 76 and into the vertebra to secure the associated blade 12, 16 to the vertebra.

The mounting rails 20, 92, 94, 96 have features for rapidly engaging and disengaging the retractor blades 12, as shown in FIGS. 3 and 3A. For example, the mounting rail 20 has a lower base 110 and an upper flange 112, the flange 112 having two elongate sections 114, 116 separated by the elongate groove 70 therebetween. The elongate sections 114, 116 have integral resilient arms 30, 32 that frictionally engage inner slot surfaces 193, 195 (see FIG. 5) of the retractor blade 12 to resist removal of the blade 12 from the guide dilator 10. The guide dilator 10 also has mounting rails 92, 96 that are substantially similar to the mounting rails 20, 92 with the exception that the mounting rails 92, 96 are not intersected or divided by the grooves 70, 72. Instead, the mounting rail 92 has a lower base 120 and an upper flange 122 with resilient arms 134, 136 substantially similar to the arms 30, 32. Surrounding the lower base 120 of the mounting rail 92 is a recessed surface 138 that provides additional clearance for the retractor blade 14 to slide onto the mounting rail 92.

Figure 4:
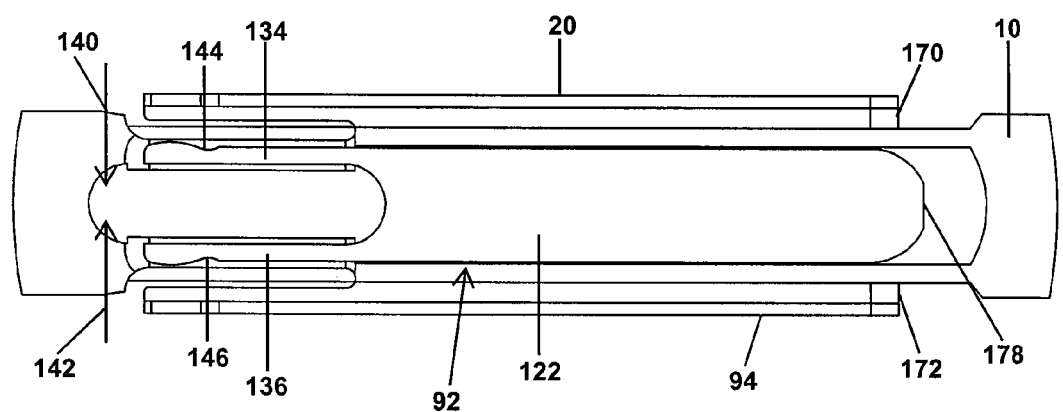
FIG. 4 is an enlarged, side elevational view of the mounting rails of the guide dilator of FIG. 1 showing resilient members of the mounting rails.
Figure 6:
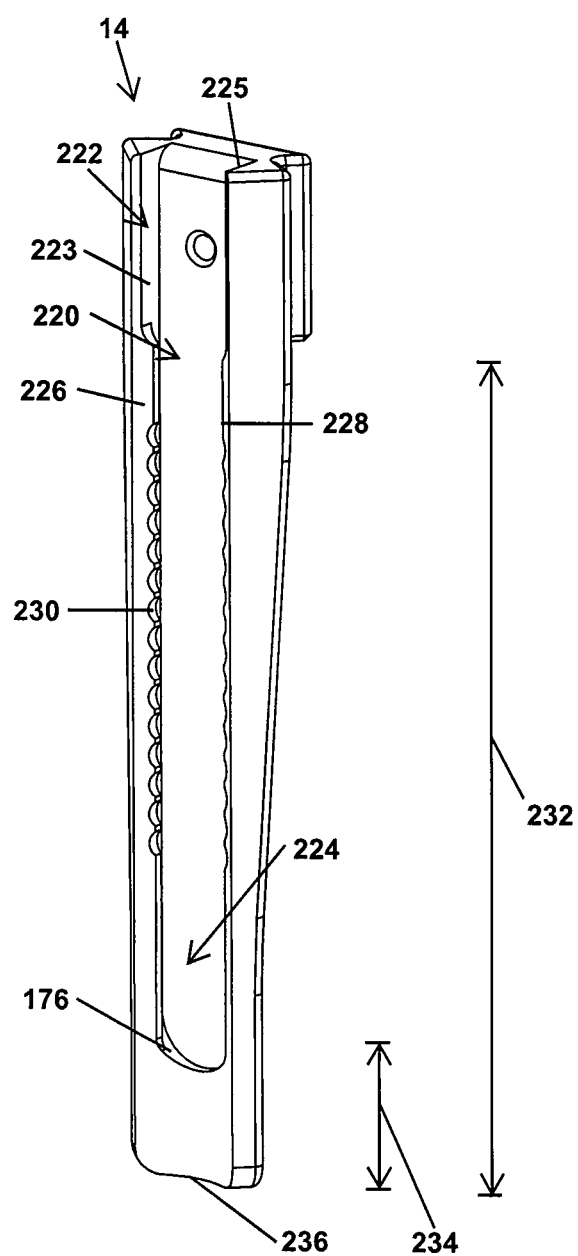
FIG. 6 is a perspective view of another one of the retractor blades of FIG. 1 showing a slot of the blade for slideably receiving a mounting rail of the guide dilator, the retractor blade of FIG. 6 lacking a cannula similar to the retractor blade of FIG. 5.

With reference to FIGS. 4 and 6, the resilient arms 134, 136 engage the slot 220 of the blade 14. The resilient arms 134, 136 have tapered surfaces 144, 146 that frictionally engage slot surfaces 223, 225 of the blade 14 and resist removal of the blade 14 from the mounting rail 92. When the blade 14 is connected to the mounting rail 92, the resilient arms 134, 136 are resiliently deflected toward each other in directions 140, 142 such that the resilient arms 134, 136 bias the tapered surfaces 144, 146 into frictional engagement with the slot surfaces 223, 225.

The guide dilator 10 and the retractor blades 12, 14, 16, 18 preferably have cooperating stop portions which limit sliding of the retractor blades beyond a position where the retractor blades 12, 14, 16, 18 are fully engaged with the mounting rails 20, 92, 94, 96. For example, with reference to FIG. 4, the mounting rails 20, 94 have lower end walls 170, 172 which abut stop surfaces on the blades 12, 16, such as the stop surface 174 of the blade 12 (see FIG. 5). The lower end walls 170, 172 have curvatures that are complimentary to the stop surfaces of the blades 12, 16 which permits the surfaces to firmly engage the end walls 170, 172. The mounting rails 92, 96 have similar lower end walls 178, 180 for engaging stop surfaces on the retractor blades 80, 82, such as a stop surface 176 of the blade 14 (see FIG. 6).

Figure 5A:
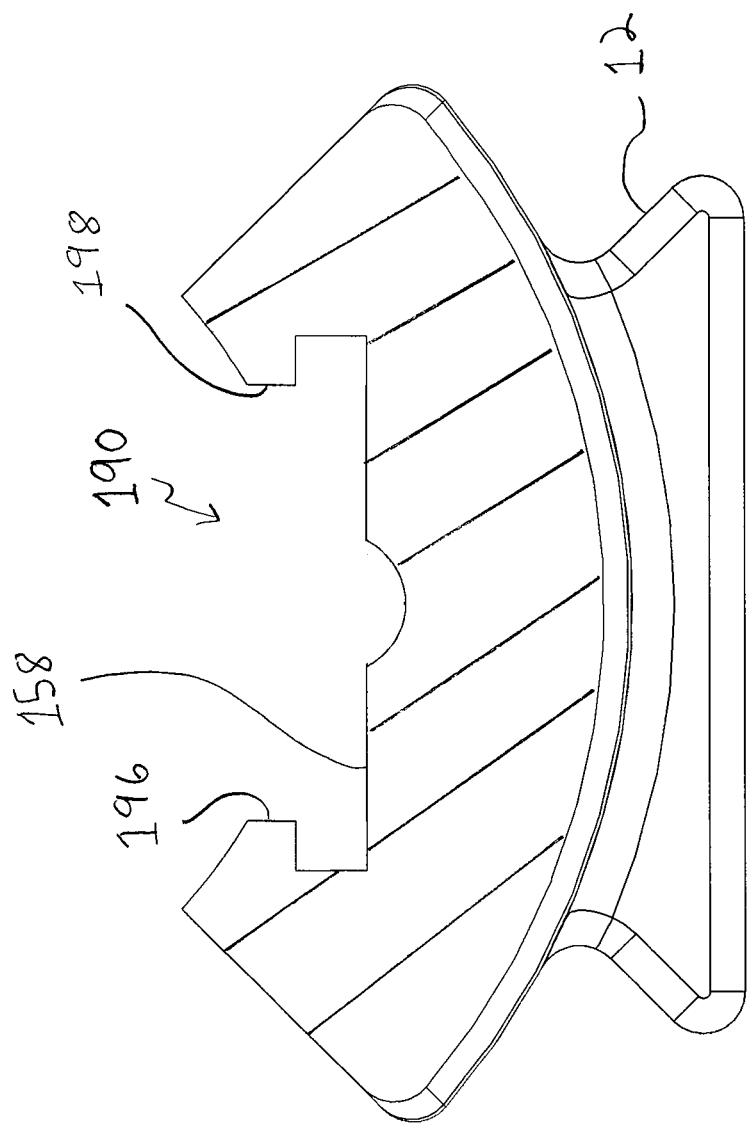
FIG. 5A is a cross-sectional view taken across the line 5A-5A in FIG. 5A

As shown in FIGS. 5 and 5A, a cannulated blade, such as the blade 12, has a slot 190 for receiving the flange 112 of the mounting rail 20. The slot 190 comprises an open end 192 and a closed end 194, the mounting rail 20 being inserted into the open end 192 of the slot 190 and slid along the blade 12 until reaching the closed end 194 of the slot 190. The blade 12 has inwardly extending walls 196, 198 which slide beneath the flange 112 and interlock therewith to restrict movement of the blade 12 radially outward from the guide dilator 10. In one form, axially extending surfaces of the flange 112 and the walls 196, 198 extend from a midline 199 of the blade 12 toward the distal end 36 of the blade 12 a distance that is at least a quarter of a blade length 210 (see FIG. 5) when the blade 12 is connected to the guide dilator 10. The walls 196, 198 have serrations 200, 202 for engaging ratchet arms 203, 205 of a docking anchor 201 (see FIG. 31) which may be inserted into the open end 192 of the slot 190 and slid down toward the closed end 194 with the ratchet arms 203, 205 resiliently biased into engagement with the serrations 200, 202 to releasably fix the depth of the docking anchor 201 within the blade 12.

Further, even if the retractor blades 12, 14, 16, 18 have varying straightness along their lengths, sliding the blades 12, 14, 16, 18 fully onto the mounting rails 20, 92, 94, 96 (see FIG. 1) holds distal ends 34, 35, 37, 39 of the blades 12, 14, 16, 18 to the guide dilator 10. The interlocking engagement between the flanges of the mounting rails, such as the flange 112 of the mounting rail 20, and the inwardly extending walls of the associated blade, such as walls 196, 198 of the blade 12, ensures that the walls 196, 198 are held below the flange 112 when the stop surface 174 is slid into engagement with the lower end wall 170 of the mounting rail 20. With the walls 196, 198 held firmly adjacent the lower base 110 of the mounting rail 20, the blade distal end 34 extends from the lower end wall 170 of the mounting rail 20 along the leading end portion 42 of the guide dilator 10. In this manner, the guide dilator 10 compensates for variation in the straightness of the retractor blades 12, 14, 16, 18 by ensuring the retractor blade distal ends 34, 35, 37, 39 are evenly spaced about the guide dilator 10 and spaced from each other.

The blade length 210 is chosen for a particular operation and typically is in the range of 80 mm-180 mm for lateral approach surgery. As shown in FIG. 5, the blade 12 also has a tip distance 216 extending between the stop surface 174 and the distal end 34. When the blade 12 is slid onto the mounting rail 20 and the lower end wall 170 of the mounting rail 20 abuts the stop surface 174 of the blade 12, the blade 12 generally extends the tip distance 216 along the leading end portion 42 of the guide dilator 10 beyond the stop surface 174 (see FIG. 3).

The blade 14 is substantially similar to the blade 12 with the exception of the cylindrical portion 64 and the cannula 74 thereof. Like the blade 12, the blade 80 has a slot 220 with an open end 222, a closed end 224, and inwardly extending walls 226, 228 with serrations 230. The blade 14 has a length 232 and a tip distance 234 extending between the stop surface 176 and a distal end 236 of the blade 14. The guide dilator 10 may be provided with sets of blades 12, 14, 16, 18 having different blade lengths 210 or 232, although the tip distance 216 or 234 remains similar for the different blade lengths. In this manner, the amount of leading end portion 42 covered by the blades 12, 14, 16, 18 is fixed for different sets of blades having different lengths.

Figure 7:
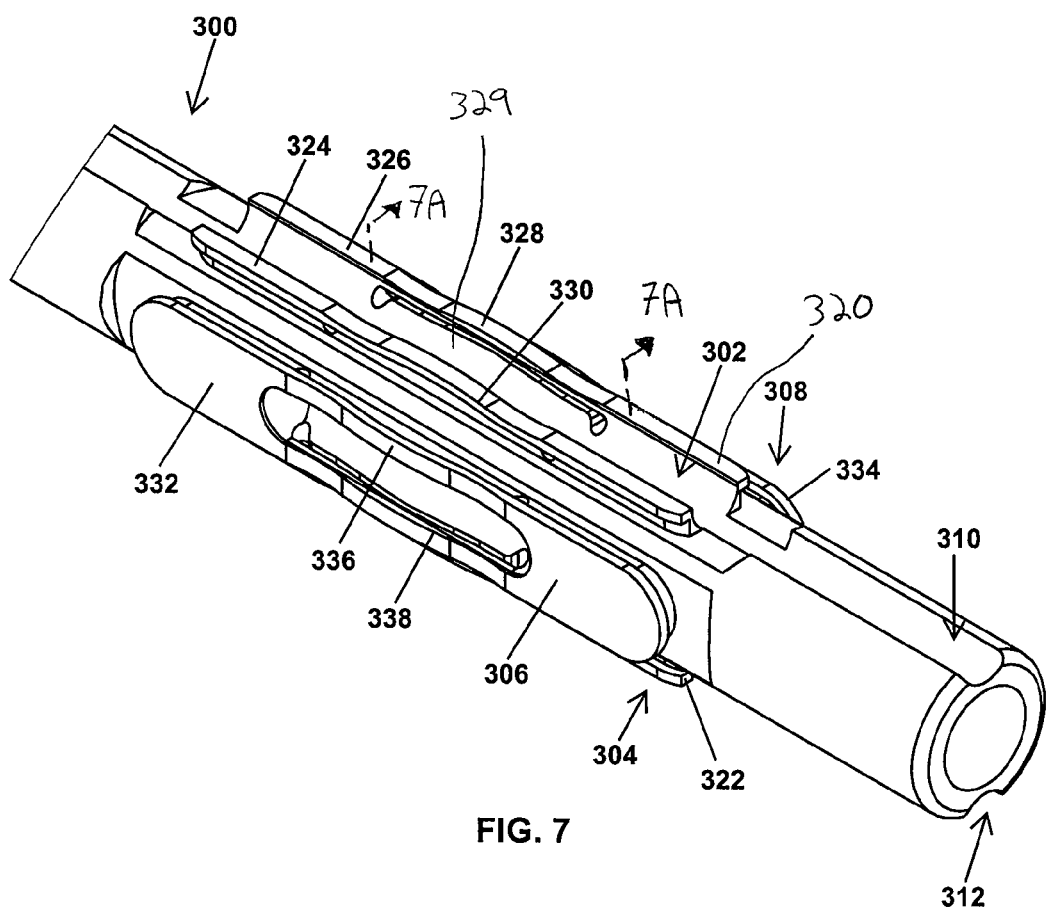
FIG. 7 is an enlarged, perspective view of a leading end of a guide dilator in accordance with another form of the present invention showing mounting rails of the guide dilator.

A guide dilator 300 in accordance with another form of the present invention is illustrated in FIG. 7. The guide dilator 300 is substantially similar to the guide dilator 10 previously discussed, with the exception that the guide dilator 300 has mounting rails 302, 304, 306, 308 with different mechanisms for retaining the respective retractor blades than the guide dilator 10. More specifically, the mounting rails 302, 304, which are intersected by grooves 310, 312, have flanges 320, 322 with elongate sections 324, 326 and resilient members 328, 330 disposed in the middle of the elongate sections 324, 326. The resilient members 328, 330 are resiliently biased radially outward into engagement with associated retractor blades to provide a frictional engagement therebetween in a manner similar to the resilient arms 30, 32. Likewise, the mounting rails 306, 308 have flanges 332, 334 with resilient members 336, 338 for creating frictional engagement with associated retractor blades.

As shown in FIG. 7A, the resilient member 328 of the mounting rail 302 is spaced from a lower portion 329 of the rail 302 by a gap 331 when a retractor blade is not connected to the mounting rail 302. Sliding a retractor blade onto the rail 302, such as blade 12, deflects the resilient member 328 radially inward in direction 333 and decreases the size of the gap 331, as shown in FIG. 7B. With the retractor blade 12 connected to the rail 302, the resilient member 328 biases against a surface 335 thereof radially outward in direction 337 into frictional engagement with a surface 158 of the blade 12 (see FIG. 5). In one approach, the guide dilator 300 is made of stainless steel or aluminum and the member 328 may resiliently flex due to the elongate gap spacing 331 machined into the mounting rail 302. The retractor blade 12 may be made of, for example, aluminum or polyether ether ketone (PEEK).

Figure 8:
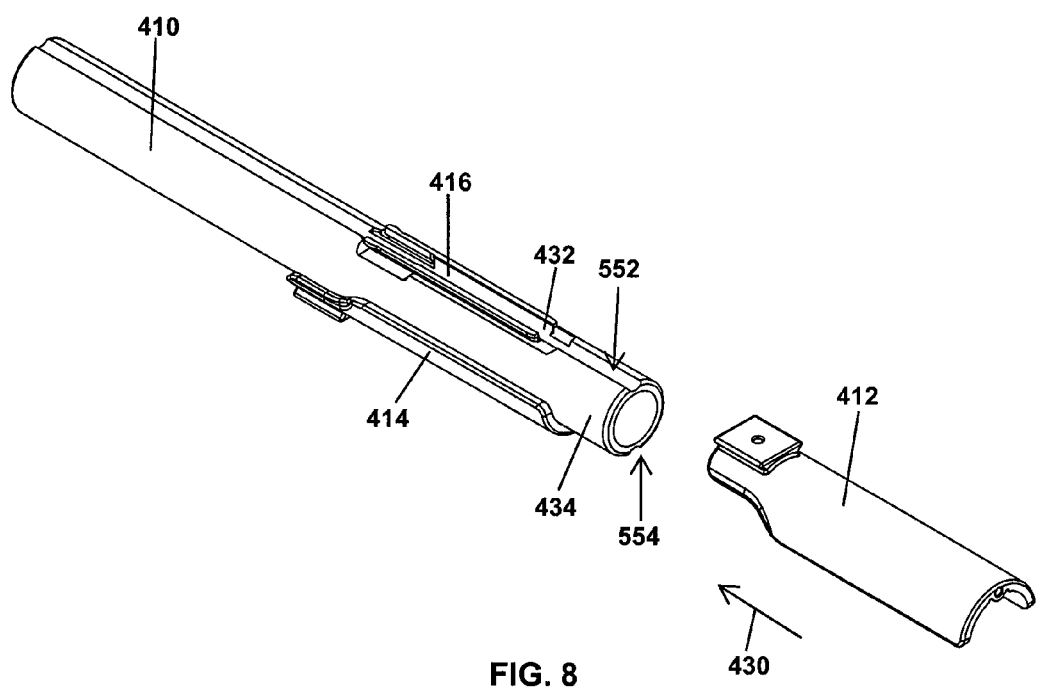
FIG. 8 is a perspective view of a guide dilator and retractor blades in accordance with another form of the present invention showing one of the retractor blades slid off of the guide dilator.
Figure 9:
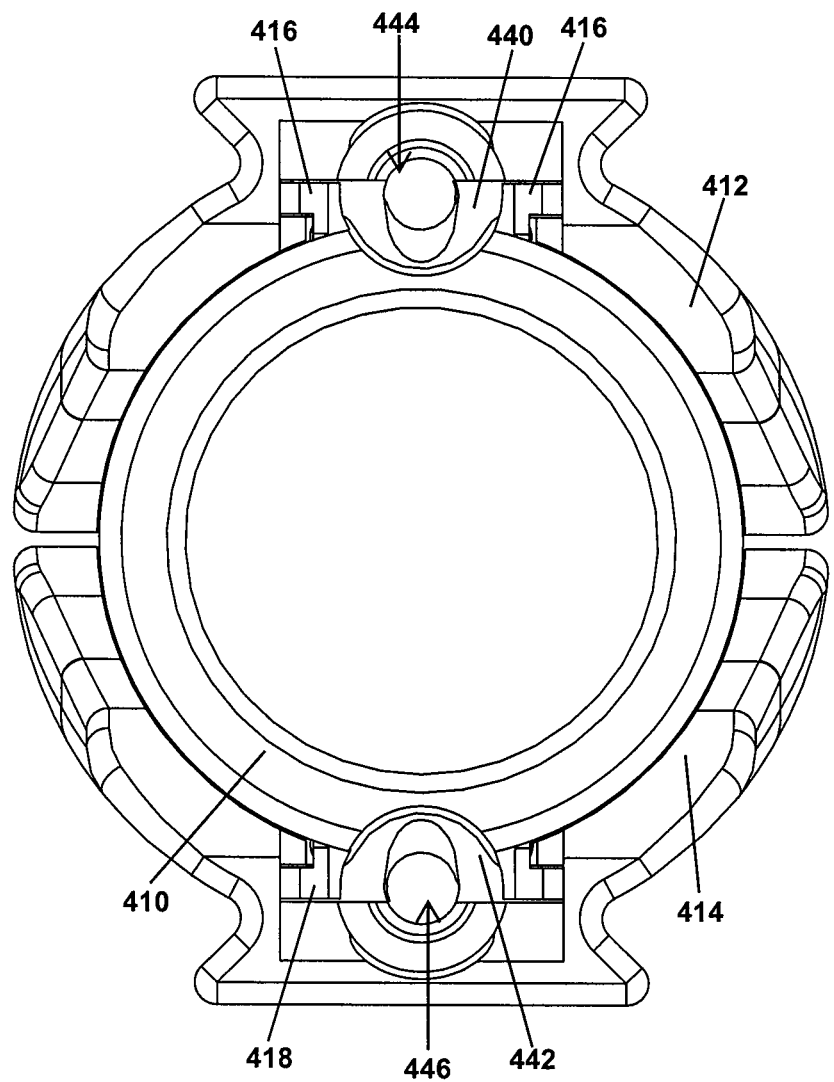
FIG. 9 is an enlarged, end view of the guide dilator of FIG. 8 with both retractor blades connected to the guide dilator showing an outer profile of the retractor blades.
Figure 10:
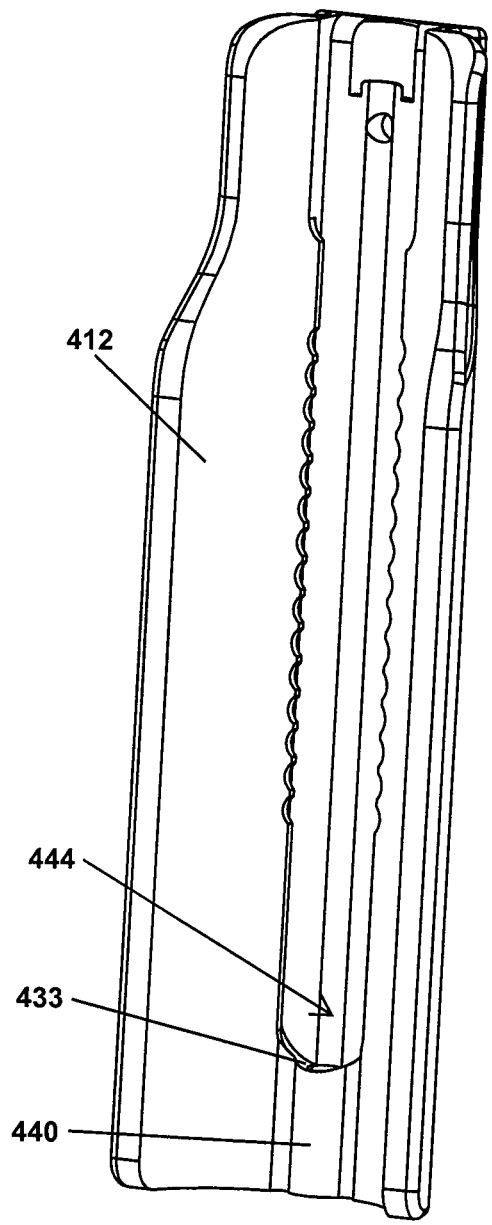
FIG. 10 is a perspective view of one of the retractor blades of FIG. 8 showing a slot of the blade for slideably receiving a mounting rail of the guide dilator.
Figure 11:
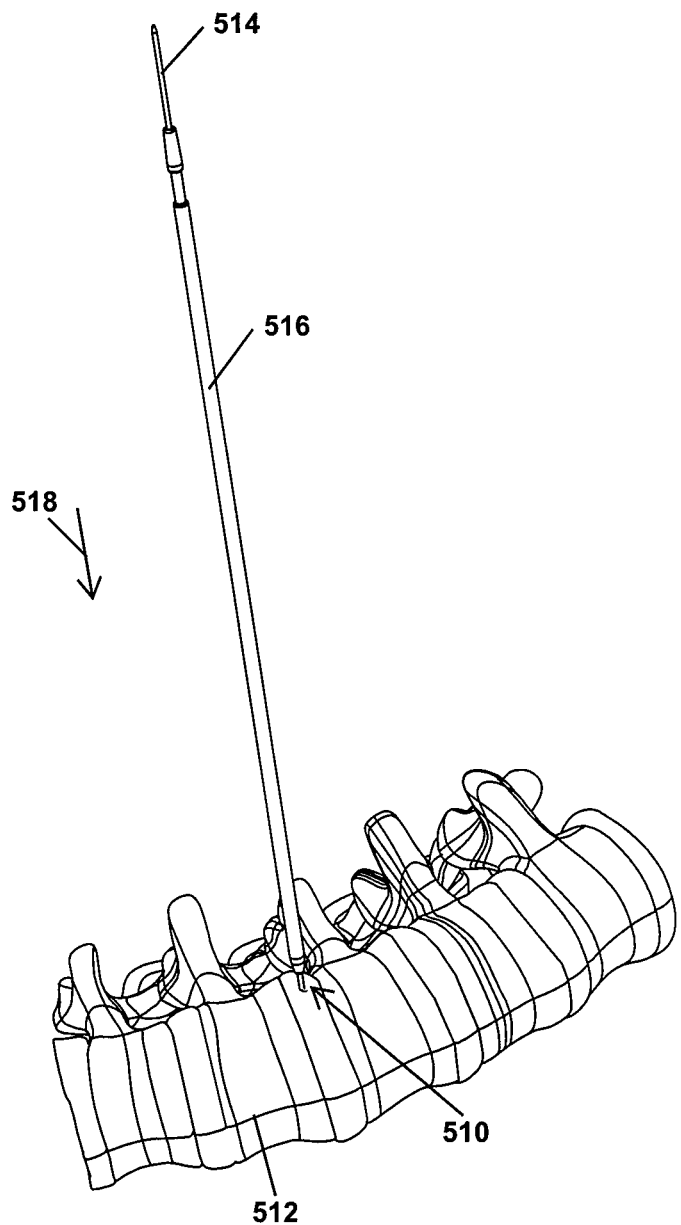
FIGS. 11-24 illustrate an exemplary method of enlarging an incision during a lateral approach surgery using the guide dilator and retractor blades of FIG. 8.

A guide dilator 410 and retractor blades 412, 414 in accordance with another form of the present invention are shown in FIGS. 8-10. The guide dilator 410 is similar to the guide dilator 10 and has mounting rails 416, 418 (see FIG. 9) for slideably engaging the blades 412, 414. Specifically, the blades 412, 414 slide onto the mounting rails 416, 418 in direction 430, as shown in FIG. 8. For example, blade 412 slides in direction 430 into engagement with mounting rail 416 and may slide in direction 430 until a stop surface 433 (see FIG. 10) engages a lower end wall 432 of the mounting rail 416. The blades 412, 414 may be easily and rapidly slid onto or off of the guide dilator 10 along a leading end portion 434 thereof.

Turning to FIG. 9, the blades 412, 414 form a generally circular profile when engaged with the guide dilator 410. One difference between the guide dilator 410 and the guide dilator 10 is that the guide dilator 410 has only two mounting rails 416, 418 to accommodate blades 412, 414 which each extend around the guide dilator 410 approximately 180 degrees. Another difference is that the blades 412, 414 are both cannulated with a cylindrical portion 440, 442 and cannulas 444, 446 sized to receive a fixation pin, nerve probe, or other instrument as will be discussed in greater detail below.

Figure 12:
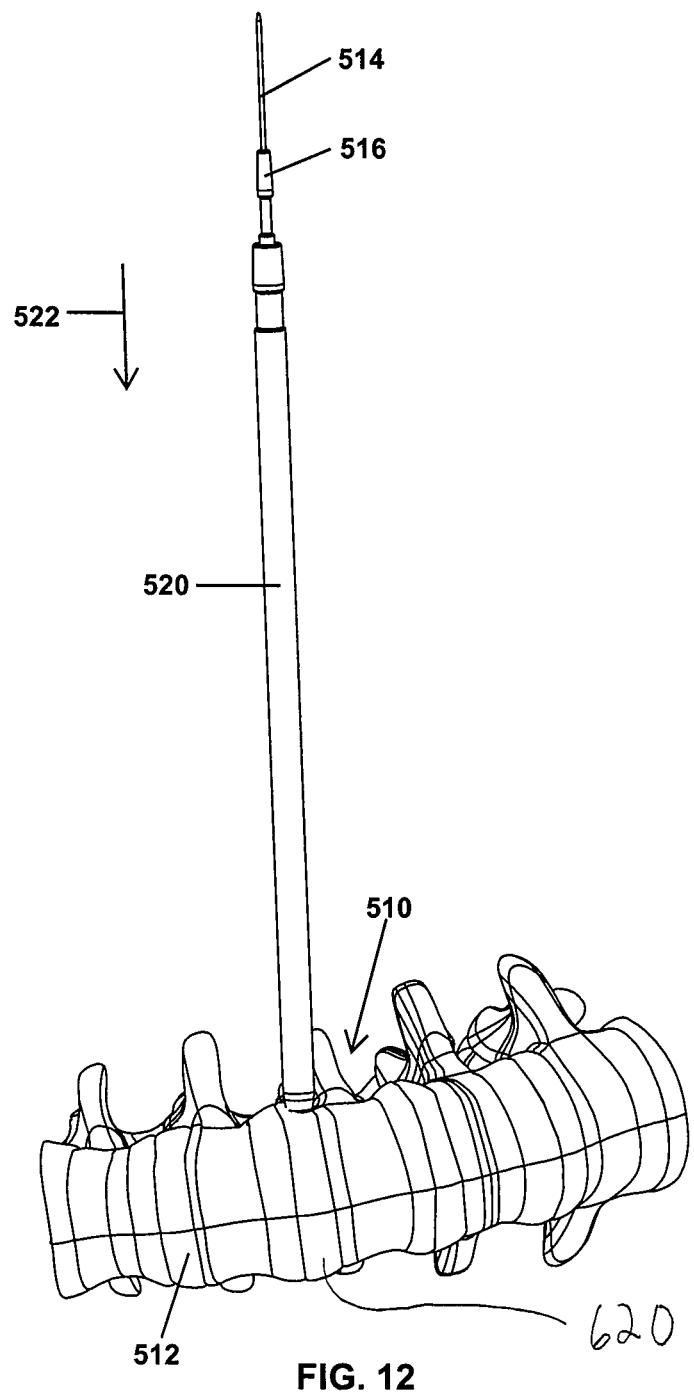
Figure 13:
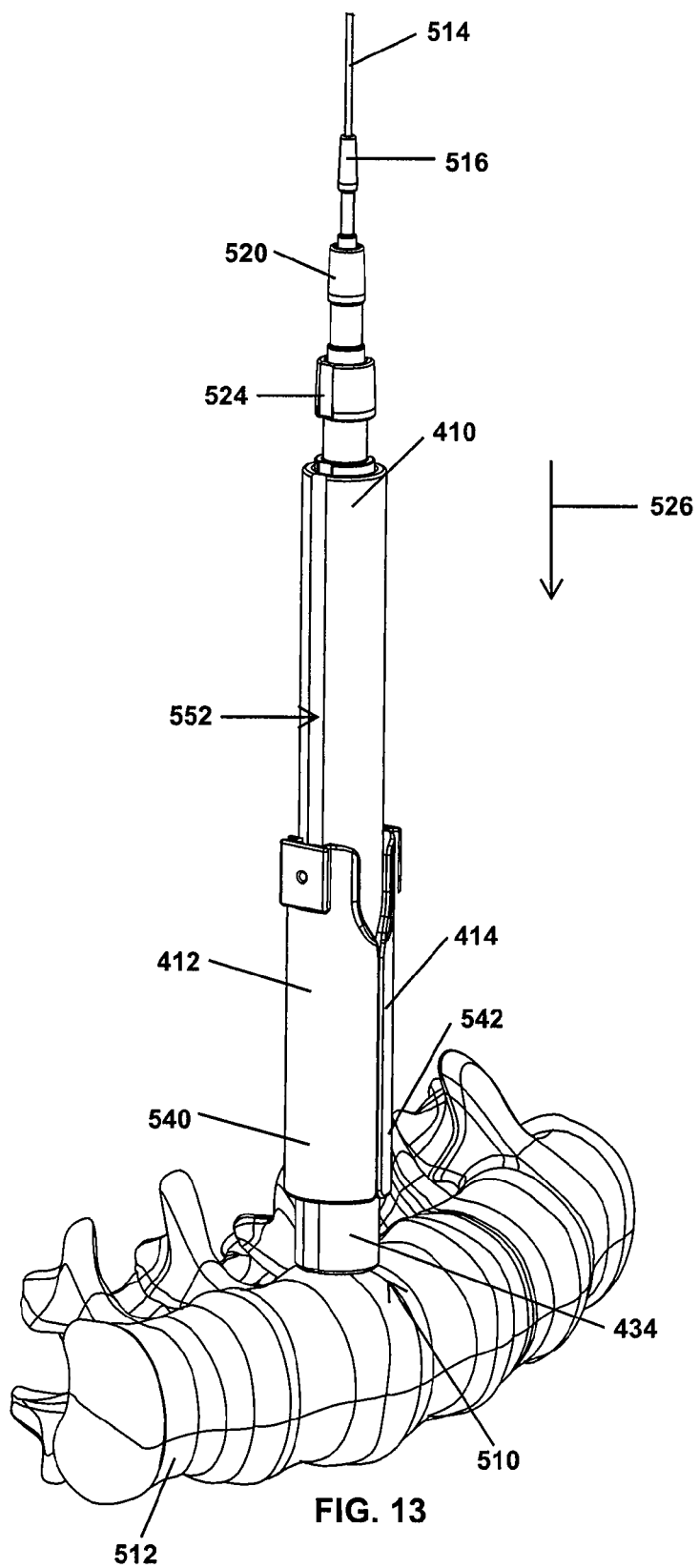
Figure 14:
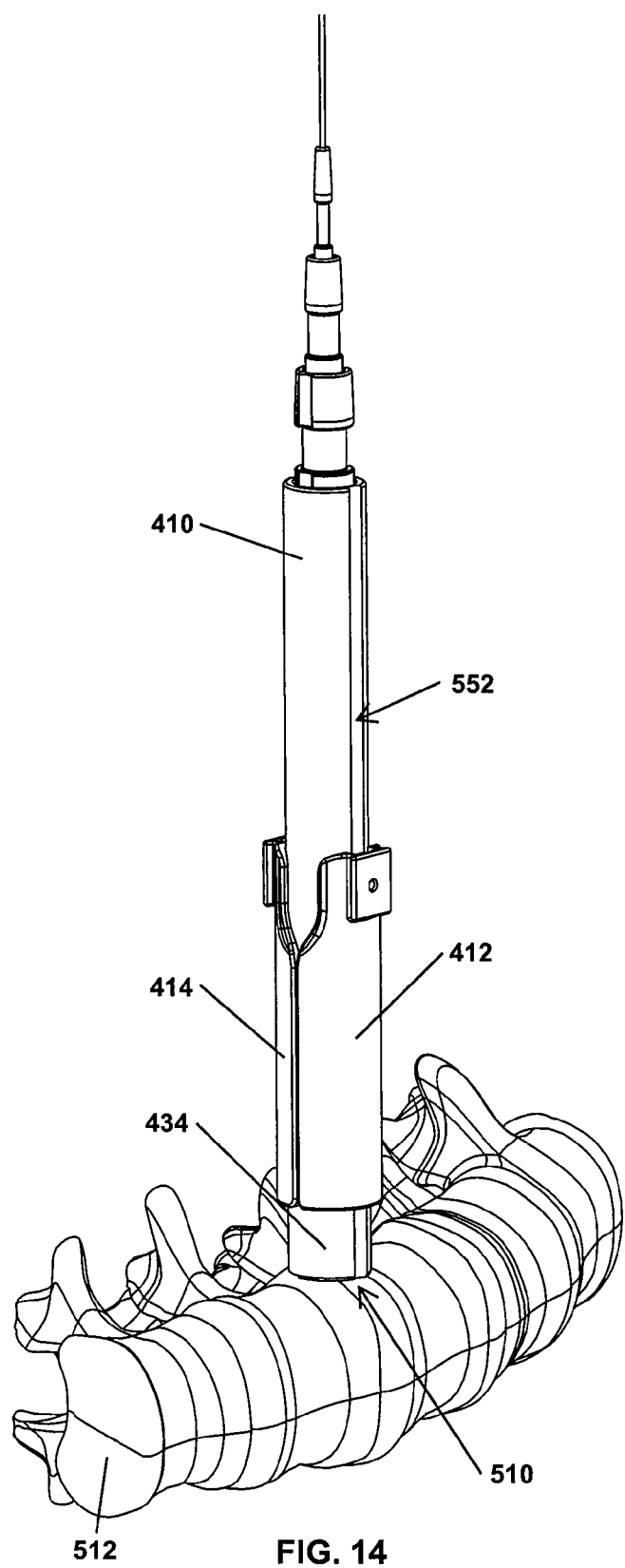
Figure 15:
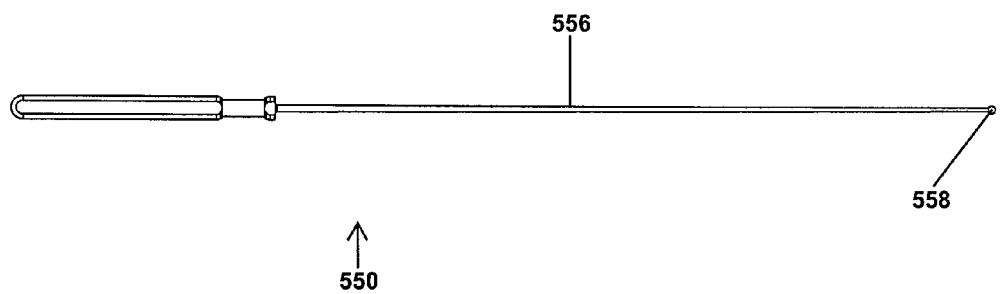
Figure 16:
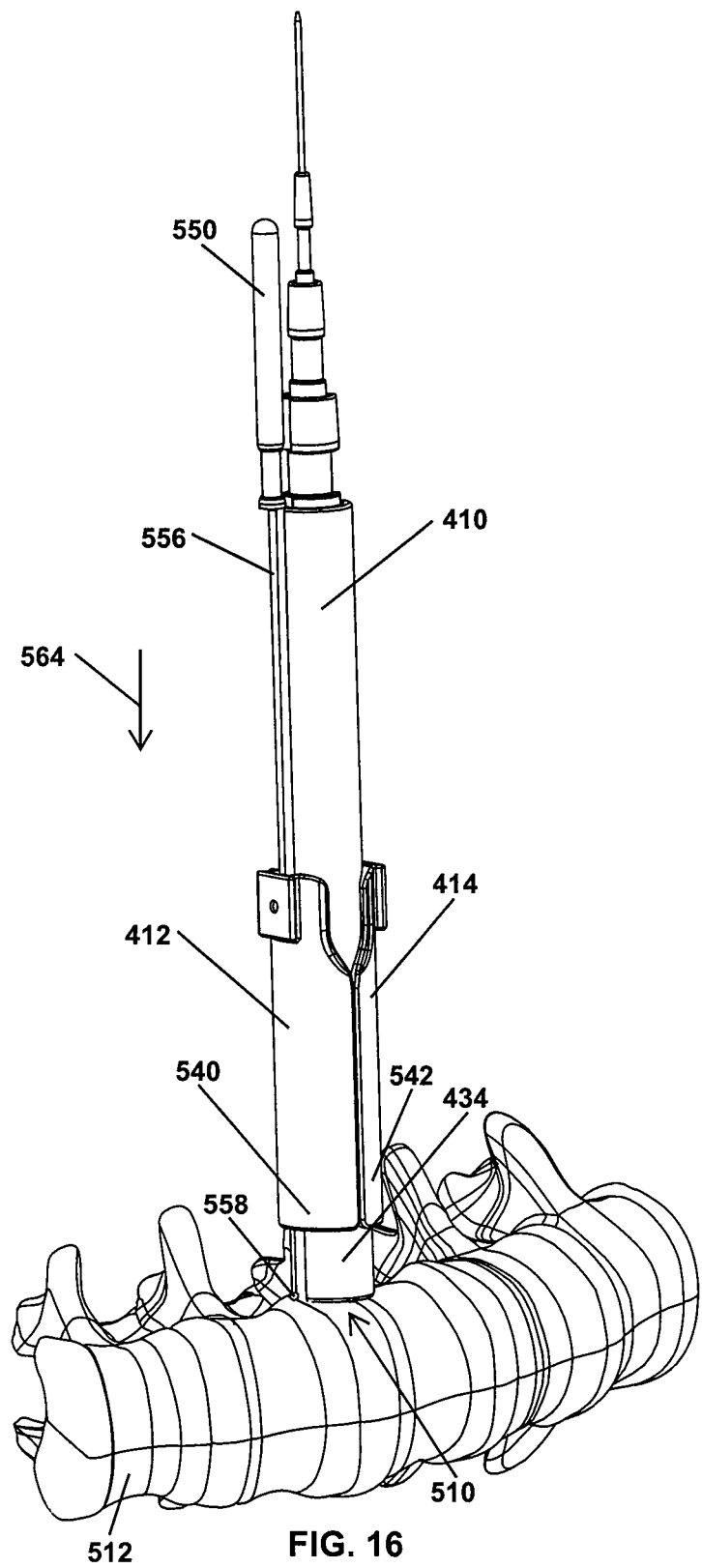

Referring next to FIGS. 11-24, a retraction procedure using the guide dilator 410 and the blades 412, 414 is illustrated. Initially, an incision is made adjacent a desired surgical site 510 of a spine 512. A dilator 516 is inserted in the incision into position at a surgical site 510, such as into contact with the intervertebral disc 620. A guide wire 514 is inserted into the cannula of the dilator 516 in direction 518 until the guide wire pierces into the intervertebral disc 620, securing the position of the dilator 516. As shown in FIG. 12, a second dilator 520 is slid downward along the first dilator 516 in direction 522 to further dilate the tissues surrounding the surgical site 510. A third dilator 524 may be slid over the second dilator 520 to further expand the tissues, as shown in FIG. 13. Once the dilators 516, 520, 524 have initially enlarged the incision, the assembled guide dilator 410 and the retractor blades 412, 414 may be slid along the dilator 524 in direction 526 into the incision. As is apparent, the leading end portion 434 of the guide dilator 410 enlarges the tissues surrounding the incision as the leading end portion 434 is advanced toward the surgical site 510. Further, distal ends 540, 542 of the retractor blades 412, 414 also dilate the tissues as the distal ends 540, 542 are advanced into the incision. In some approaches, it may be desirable to insert the guide dilator 410 and connected blades 412, 414 as shown in FIG. 14 to permit retraction of the blades 412, 414 in directions generally perpendicular to the length of the spine 512.

Figure 17:
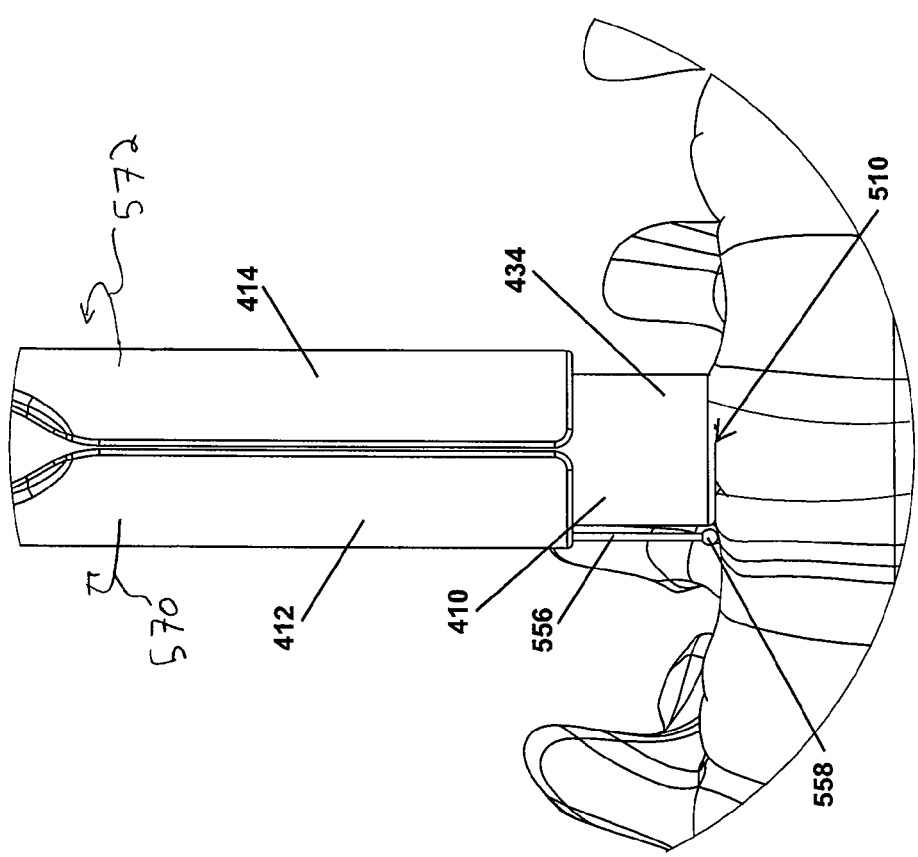

Once the leading end portion 434 of the guide dilator 410 reaches the surgical site 510, the surgeon may want to monitor for the presence of adjacent nerves before the retractor blades 412, 414 are slid downward along the leading end portion 434 into position adjacent the surgical site 510 would further dilate the tissues adjacent the surgical site 510. One approach to nerve monitoring involves advancing a nerve monitoring probe 550 (see FIG. 15) along one of the grooves 552, 554 extending along the length of the guide dilator 410 and into one of the cannulas 444, 446 (see FIG. 9) of the blades 412, 414. The nerve monitoring probe 550 has a shaft 556 ending at a bulbous tip 558 sized to fit into cannulas 444, 446 of the blades 412, 414. In the illustrated approach, the nerve monitoring probe 550 was inserted downward in direction 564 into the cannula 444 until the bulbous tip 558 extends downward beyond the tip 540 of the retractor blade 412. As shown in FIG. 17, the guide dilator 410 and the connected blades 412, 414 and nerve monitoring probe 550 may be rotated in directions 570, 572 to maneuver the tip 558 of the nerve monitoring probe 550 in a path around the surgical site 510. In this manner, the surgeon can monitor for the presence of nerves around the entirety of the leading end portion 434 before continuing the surgical procedure.

Figure 18:
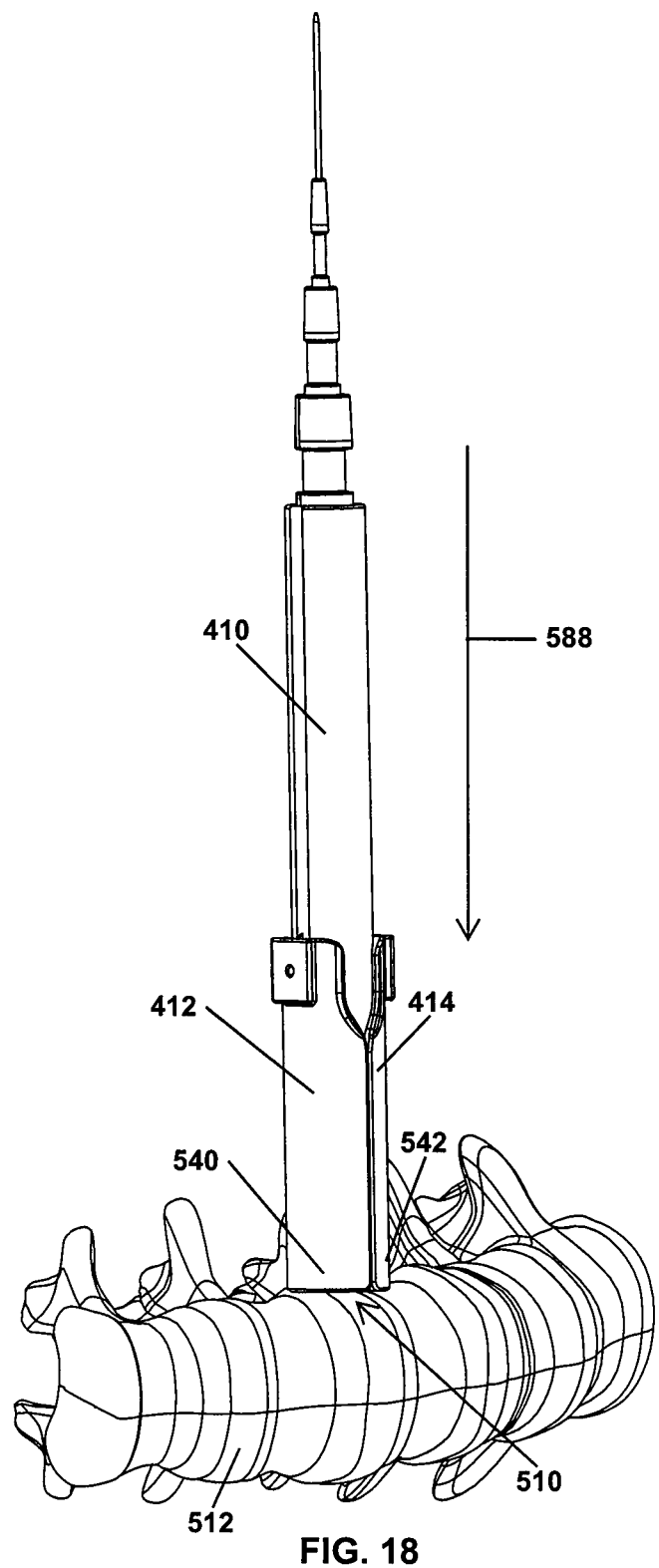
Figure 19:
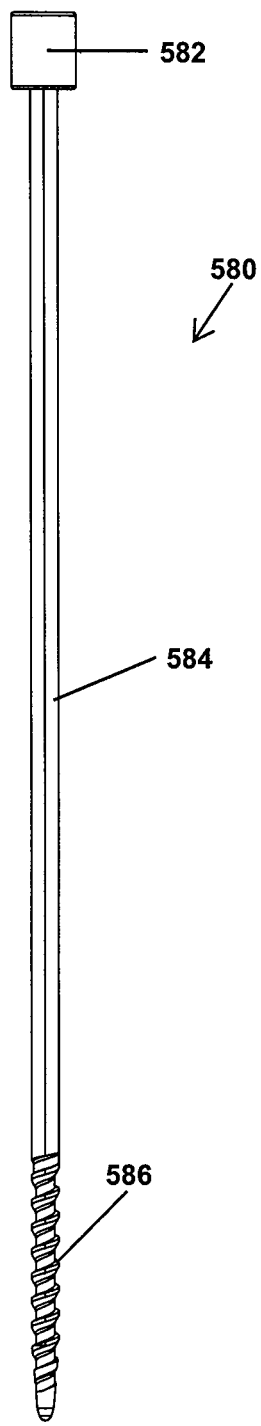
Figure 20:
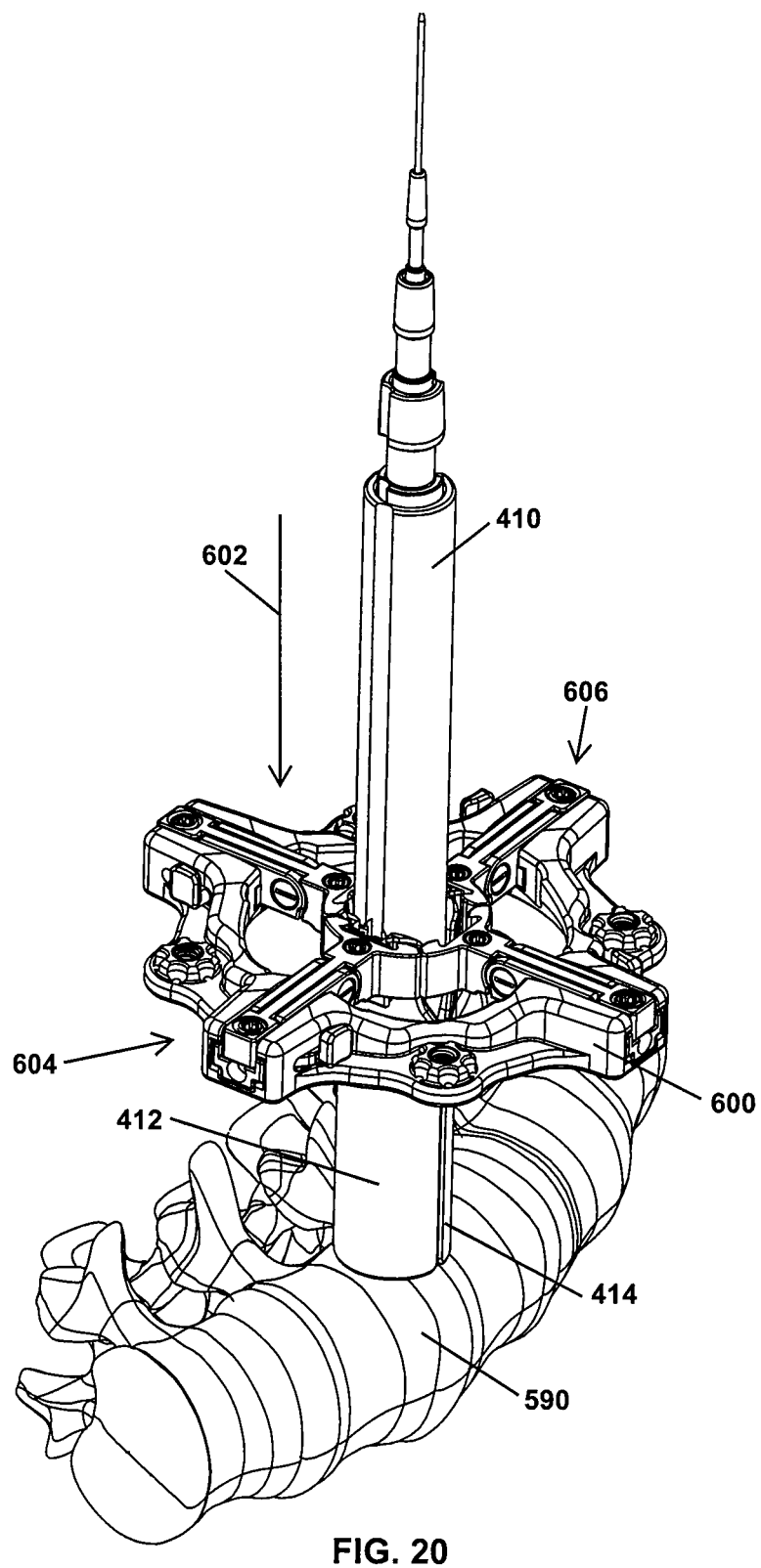

If the results of the nerve monitoring are satisfactory, the retractor blades 412, 414 are slid downwardly down the guide dilator 410 in direction 588 until distal ends 540, 542 are positioned adjacent the surgical site 510, as shown in FIG. 18. The retractor blades 412, 414 remain engaged with the mounting rails 416, 418 as the retractor blades 412, 414 slide along the leading end portion 434 of the guide dilator 410. At this point, the surgeon may want to secure the retractor blade 412 to a vertebra 590 (see FIG. 22) to stabilize the blade 412 relative to the patient during subsequent steps of the retraction procedure. In the illustrated approach, a fixation pin 580 having a head 582, a shank 584, and a tip 586 (see FIG. 19) is driven in direction 588 into the cannula 444 of the blade 412 after the nerve monitoring probe 550 has been removed from the cannula 444. With the blade 412 secured to the vertebra 590, as shown in FIG. 20, a retractor 600 is moved along the guide dilator 410 in direction 602 until operating mechanisms 604, 606 reach the blades 412, 414. As will be discussed in greater detail below, the operating mechanisms 604, 606 may be secured with the blades 412, 414 by engaging dovetail connections between the operating mechanisms 604, 606 and the blades 412, 414 and fixing the operating mechanisms 604, 606 to the blades 412, 414.

Figure 21:
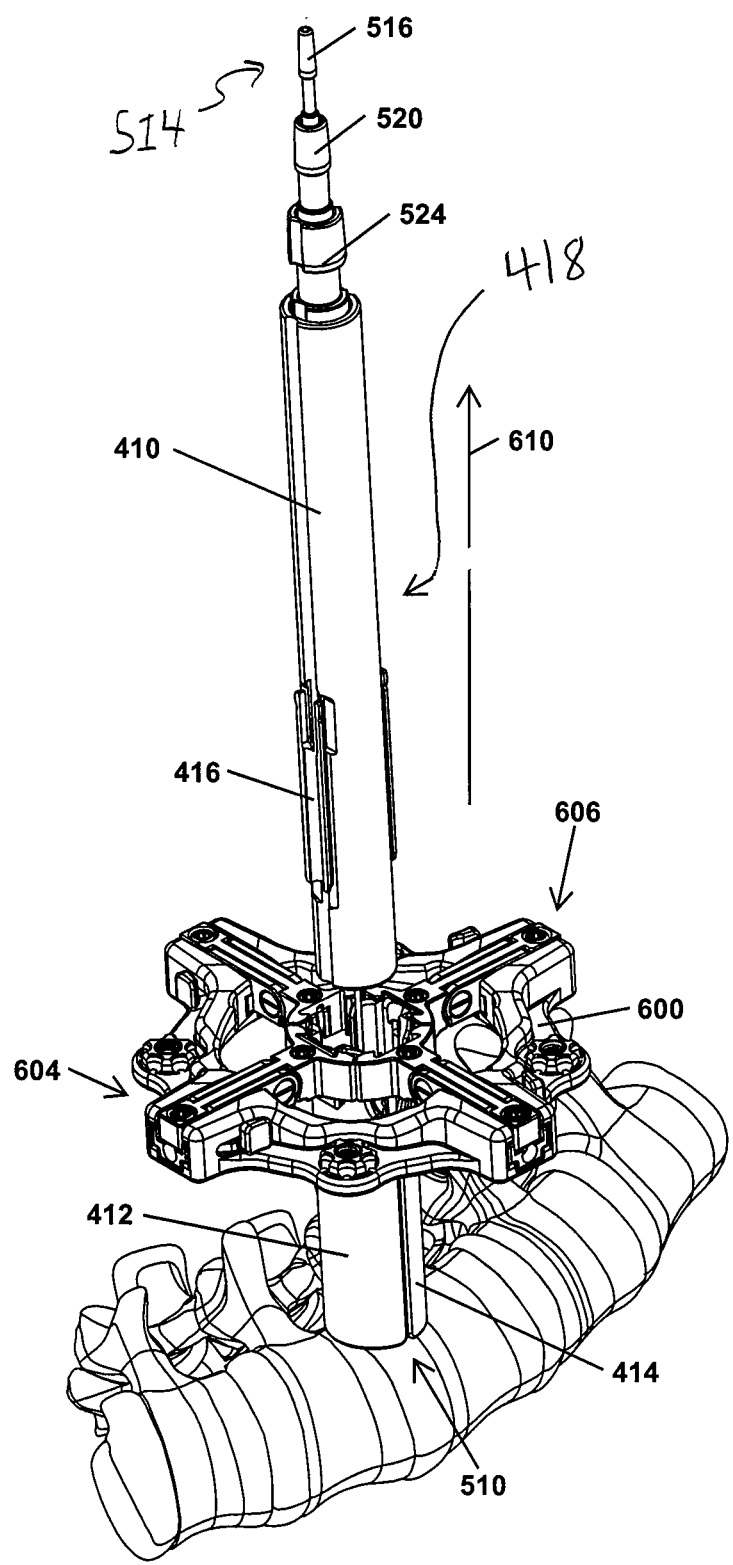

As shown in FIG. 21, the guide dilator 410, the guide wire 514, and the dilators 516, 520, 524 may be withdrawn from the incision in direction 610. With the operating mechanisms 604, 606 of the retractor 600 engaged with the blades 412, 414, the blades 412, 414 are held against movement while the guide dilator 410 is withdrawn in direction 610 outward from the incision. The relative movement between the guide dilator 410 and the retractor blades 412, 414 draws the mounting rails 416, 418 of the guide dilator 410 out of respective slots on the blades 412, 414 and disengages the connections therebetween. In this manner, withdrawing the guide dilator 410 simultaneously disengages the blades 412, 414 from the guide dilator 410 and removes the guide dilator 410 from a working channel 640 between the retractor blades 412, 414, as shown in FIG. 22.

Figure 22:
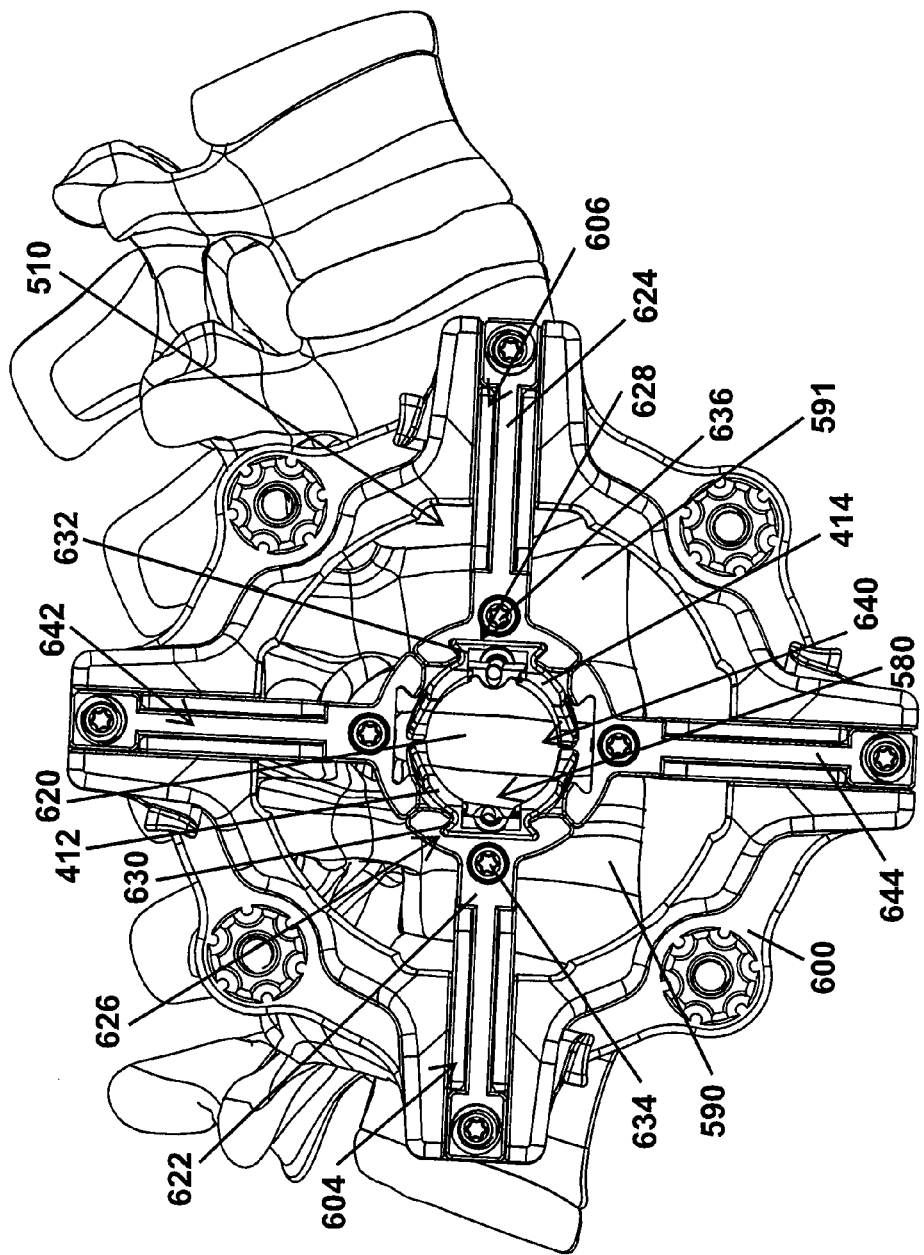
Figure 23:
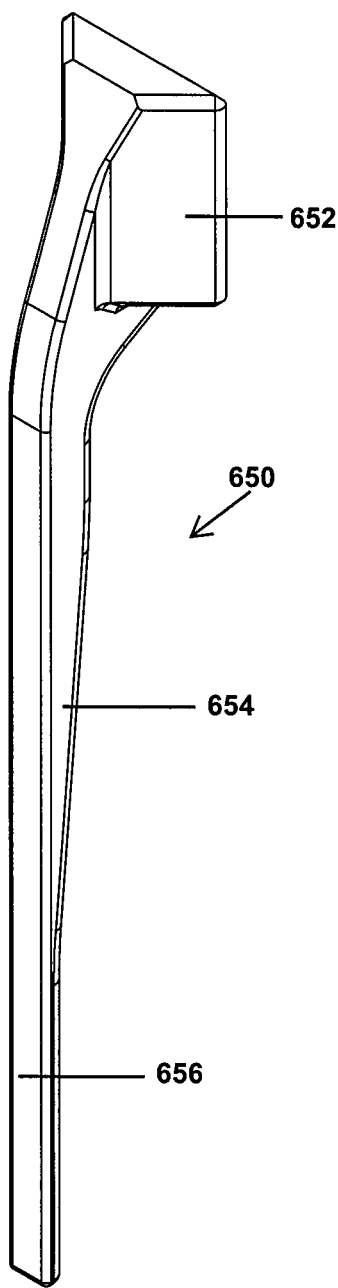
Figure 24:
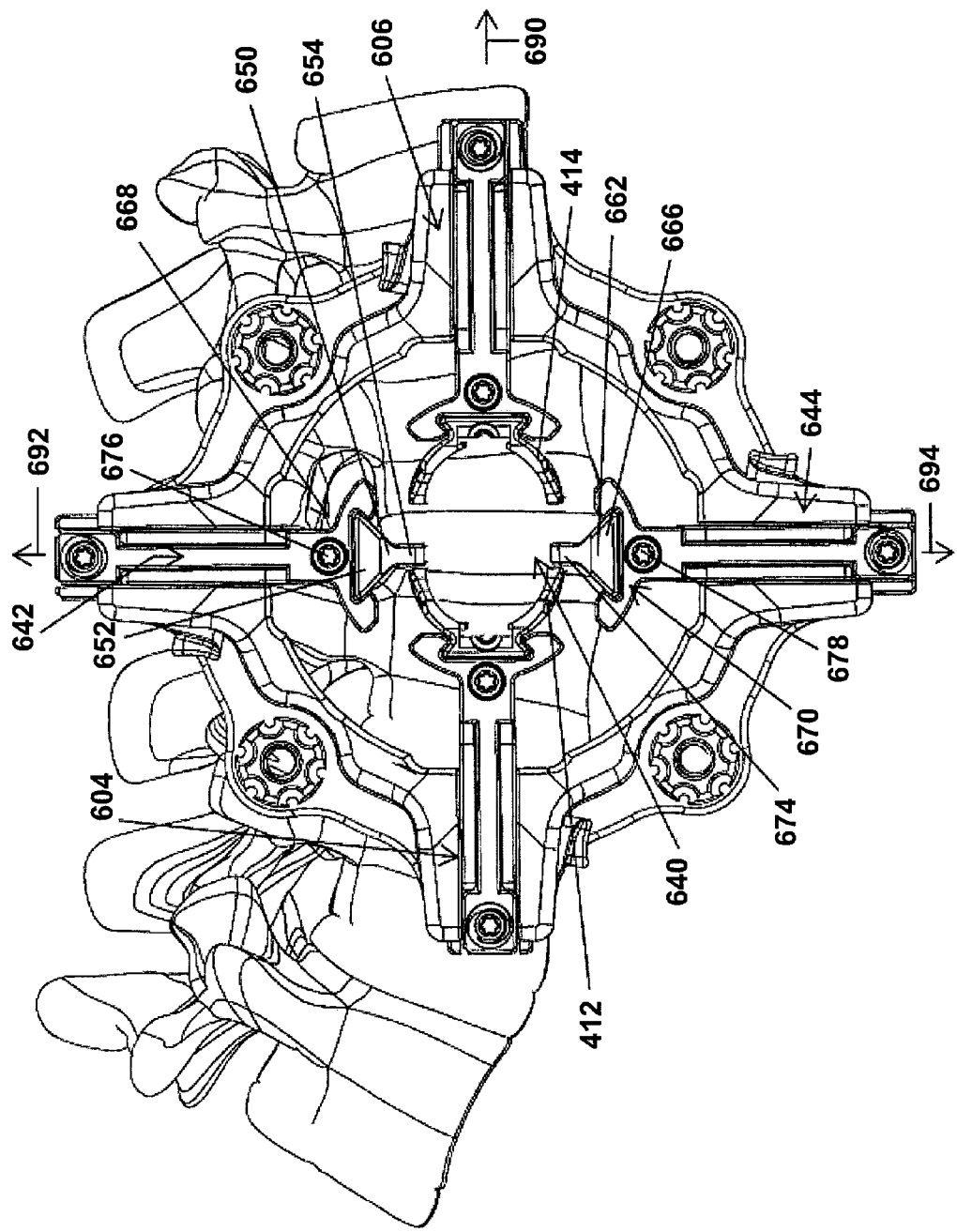

With reference to FIG. 22, the retractor 600 and the blades 412, 414 are shown positioned above the intervertebral disc 620 between vertebrae 590, 591. The operating mechanisms 604, 606 include sliders 622, 624 having dovetail recesses 626, 628 that slide over and into engagement with dovetail projections 630, 632 of the retractor blades 412, 414. The operating mechanisms 604, 606 have fixation screws 634, 636 that releasably fix the blades 412, 414 to the sliders 622, 624. As shown in FIG. 22, the retractor blades 412, 414 define an initial size of the working channel 640 to the intervertebral disc 620. To retract tissues in directions transverse to the operating mechanisms 604, 606, the retractor 600 has operating mechanisms 642, 644 that receive another pair of retractor blades such as a narrow retractor blade 650, as shown in FIG. 23. The narrow retractor blade 650 has a dovetail projection 652 and a body 654 extending from the dovetail projection 652 and ending at a tip 656. With reference to FIG. 24, narrow retractor blades 650, 662 have dovetail projections 652, 666 that are slid downward and engaged with the dovetail recesses 668, 670 with bodies 654, 674 advancing into gaps between the blades 412, 414. Fixation screws 676, 678 are tightened to engage the blades 660, 662 with the operating mechanisms 642, 644. The operating mechanisms 606, 642, and 644 are then retracted in directions 690, 692, 694 to enlarge the working channel 640 to a desired size to accommodate tools for operating on the intervertebral disc 620.

Figure 25:
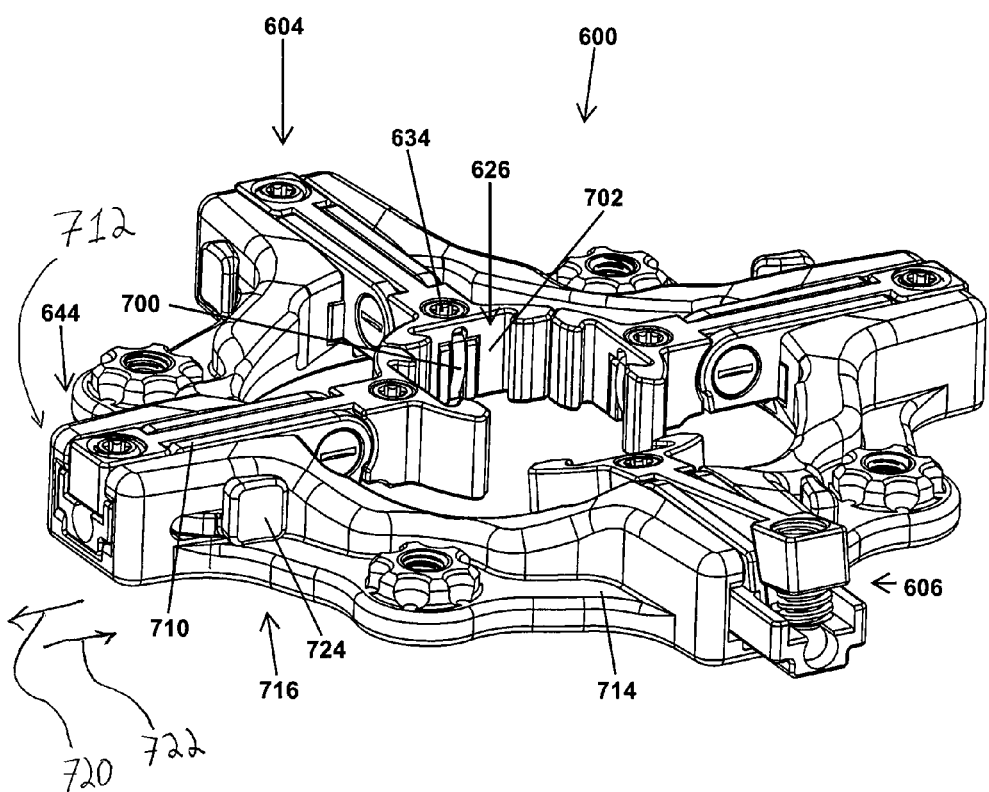
FIG. 25 is a perspective view of a retractor in accordance with one form of the present invention showing one of the sliders of the retractor in a retracted, pivoted position.
Figure 26:
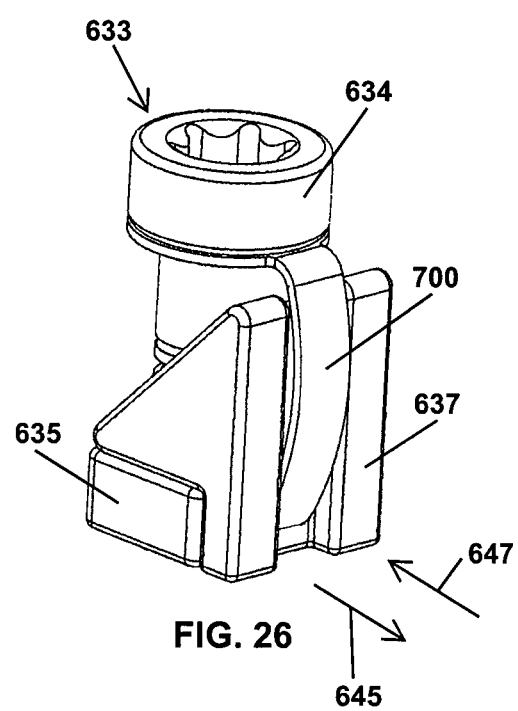
FIG. 26 is a perspective view of a wedge lock of a slider of the retractor of FIG. 25 showing the wedge lock removed from the slider.
Figure 27:
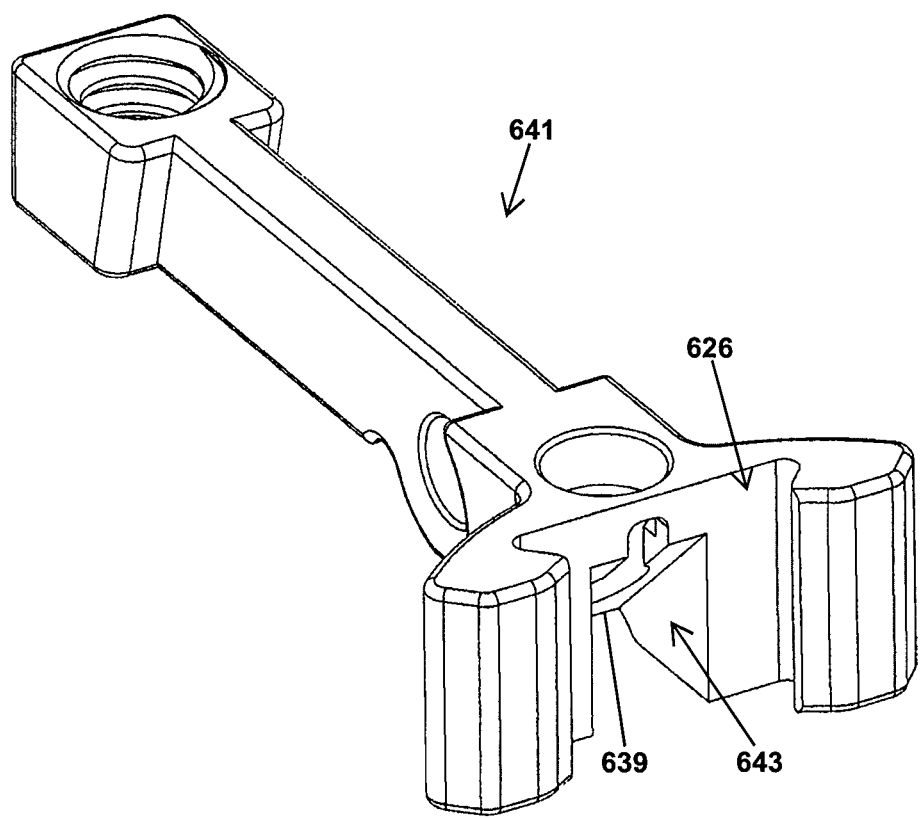
FIG. 27 is a perspective view of a slider inner member of the retractor of FIG. 25 showing the inner member removed from the retractor.

With reference to FIG. 25, the operating mechanism 604 has a resilient element 700 disposed in the dovetail recess 626 which aids in releasably securing the blade 630 to the operating mechanism 604. More specifically, the operating mechanism 604 includes a wedge lock 633 having a fixation screw 634 threadingly engaged with a nut 635, as shown in FIG. 26. The wedge lock 633 is disposed in a recess 643 of a slider inner member 641 of the operating mechanism 604, as shown in FIG. 27. Tightening the fixation screw 634 draws the nut 635 upward along the fixation screw 634 and engages wedge 637 with an inclined surface 639 of an inner member 641. Drawing the wedge 637 upward along the inclined surface 639 shifts the wedge outward in direction 645 which applies pressure against the dovetail projection 630 of the retractor blade 412 received in the dovetail recess 626 and fixes the blade 412 to the slider inner member 641. Loosening the fixation screw 634 shifts the nut 635 downward along the screw 634 and the resilient element 700 biases the wedge 637 downward and radially inward in direction 647 to return the wedge 637 to an initial, unlocked position shown in FIG. 26.

Figure 28:
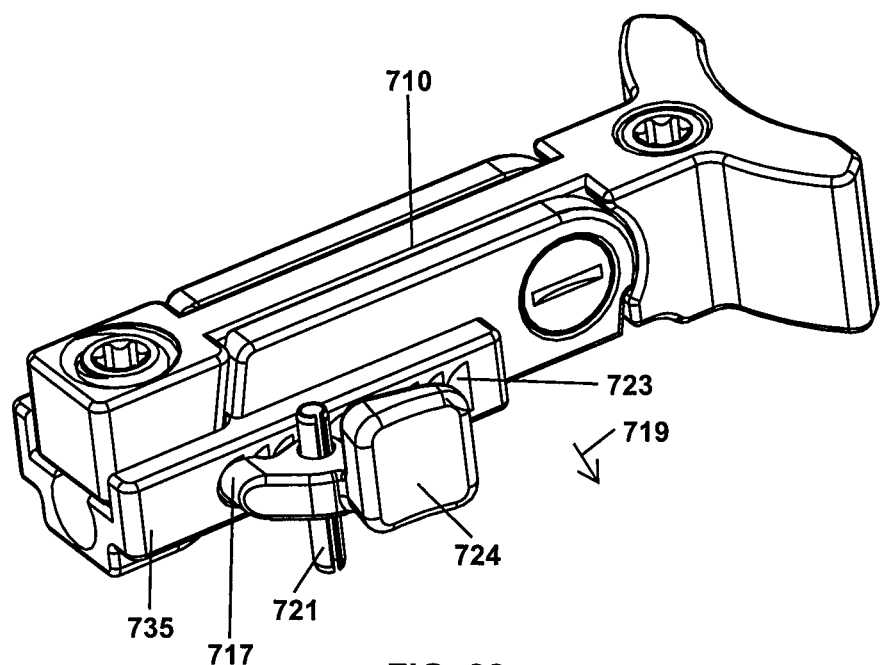
FIG. 28 is an enlarged, perspective view of a slider and portions of a ratchet mechanism of the retractor of FIG. 25 showing the slider and the ratchet mechanism portions removed from the retractor.

As shown in FIG. 25, the operating mechanism 644 includes a slider 710 disposed in a slot 712 of the retractor frame 714. The operating mechanism 644 further comprises a ratchet mechanism 716 that permits the slider 710 to retract in direction 720 but restricts return movement of the slider 710 until a button 724 of the ratchet mechanism 10 is pressed to disengage the ratchet mechanism 716 from the slider 710. With reference to FIG. 28, the slider 710 and portions of the ratchet mechanism 716 are shown removed from the frame 714 of the retractor 600. The ratchet mechanism 716 includes an integral tooth 717 of the button 724 and a spring (not shown) that biases the button 724 in direction 719 around shaft 721 and the tooth 717 into engagement with depressions 723 on a base 735 of the slider 710. Pressing the button 724 overcomes the biasing force of the spring and disengages the tooth 717 from the depressions 723 on the base 735.

Figure 29:
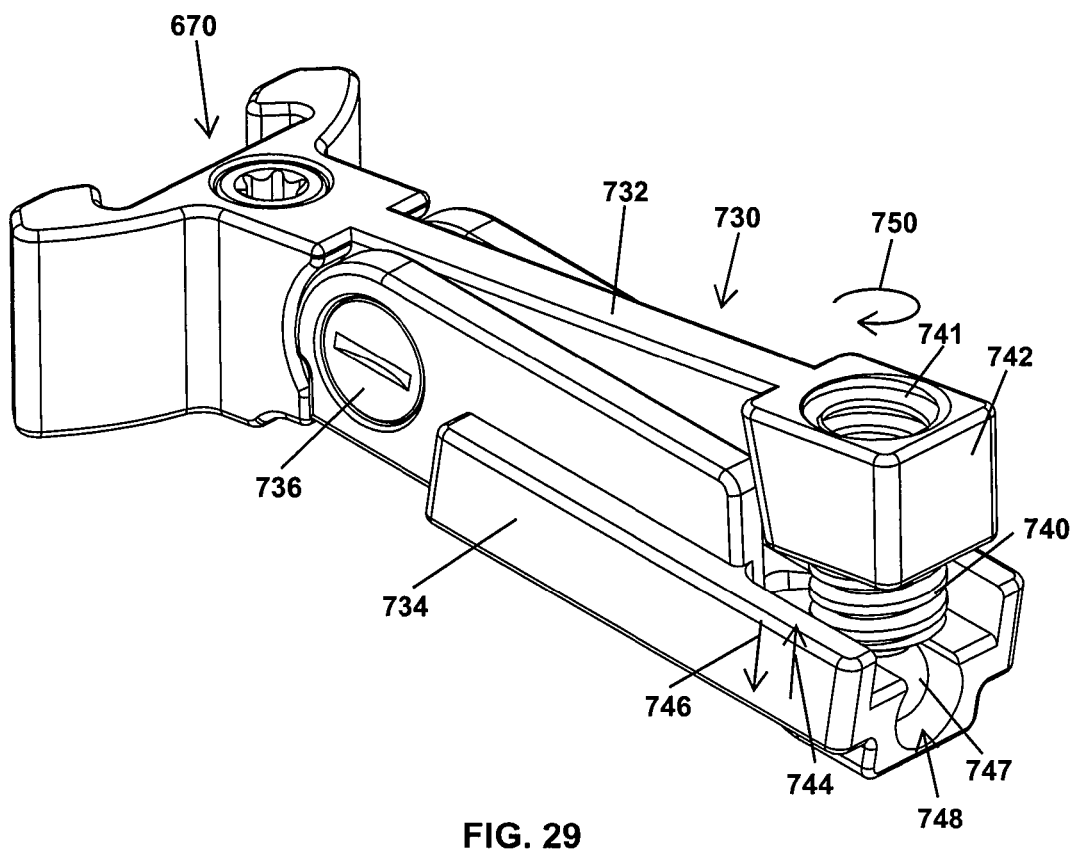
FIG. 29 is an enlarged, perspective view of a slider of the retractor of FIG. 25 showing an inner member of the slider having its rear end portion pivoted upward.

With reference to FIG. 29, the slider 730 is shown removed from the retractor frame 714. The slider 730 comprises an inner member 732 pivotally connected with a base 734 at a pivot pin 736. The slider 730 includes an elevation screw 740 engaged with threads 741 of the inner member 732. The elevation screw 740 has a ball 747 at one end thereof engaged with a socket 748 of the base 734. Rotating the elevation screw 740 in direction 750 elevates an end 742 of the inner member 732 in direction 744 and rotation of the elevation screw 740 in an opposite direction lowers the end 742 in direction 746. The connection between the ball 747 and the socket 748 permits the elevation screw 740 to rotate and elevate/lower the inner member 732 while pivoting relative to the base 734 as the inner member 732 elevates/lowers.

Figure 30:
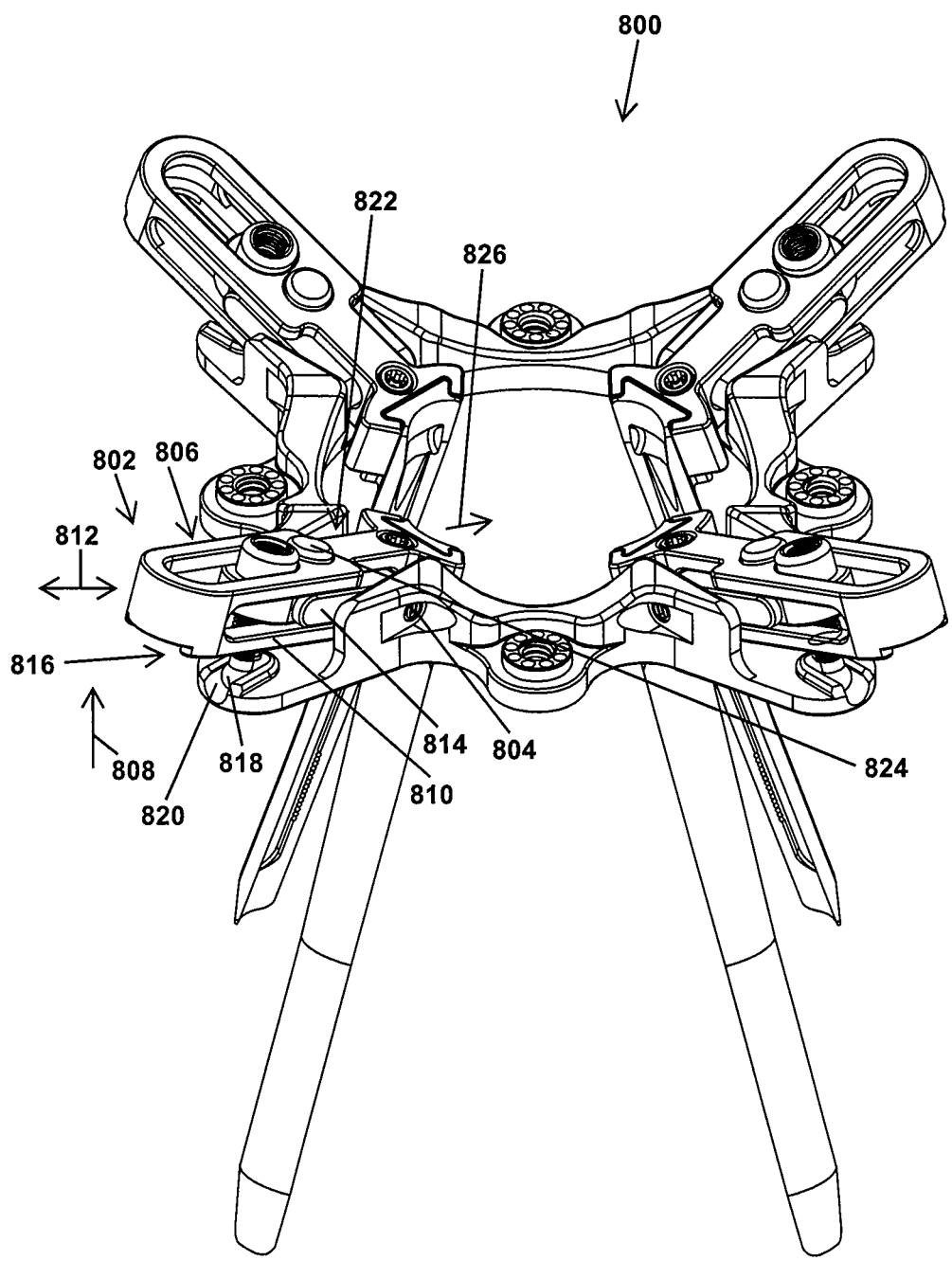
FIG. 30 is a perspective view of a retractor in accordance with another form of the present invention showing retractor blades connected to sliders which are retracted and pivoted.

With reference to FIG. 30, a retractor 800 in accordance with another form of the present invention is shown. The retractor 800 is substantially similar to the retractor 600, except for operating mechanisms 802 that have a fixed pivot pin 804 about which a slider 806 of the operating mechanism 802 pivots in direction 808. By contrast, the pivot pin 736 of the slider 750 (see FIG. 29) retracts with retraction of the slider 730. Another difference is that the slider 806 has a slider outer body 810 which slides along axis 812 relative to a slider inner body 814. Like the retractor 600, the retractor 800 has an elevation screw 816 with a ball 818 and socket 820 for accommodating pivoting of the slider 806. Further, the operating mechanism 802 includes a ratchet mechanism 822 that permits retraction of the slider 806 but restricts movement of the slider 806 in direction 826 in a manner similar to the operating mechanism 644. The ratchet mechanism 822 includes a button 824 that is pressed to disengage the ratchet mechanism 822 and permit the slider 806 to move in direction 826.

Figure 31:
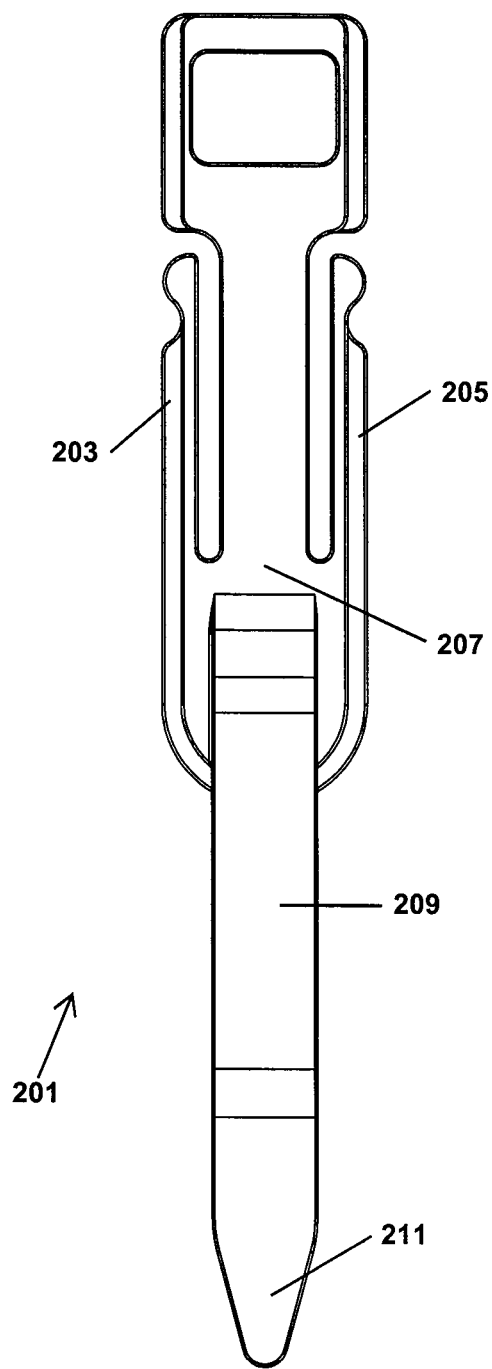
FIG. 31 is an elevational view of a retractor blade docking anchor showing a pointed tip of the docking anchor for penetrating an intervertebral disc.

With reference to FIG. 31, the docking anchor 201 has a body 207 sized to fit within a slot of a retractor blade, such as a slot 190 of the blade 12 (see FIG. 5). The body 207 is advanced into the open end 192 of the slot 190 and slid therein until reaching the closed end 194 of the slot. At this position, a blade 209 of the docking anchor 201 extends beyond the distal end 34 of the blade 12 such that a tip 211 of the blade 209 can penetrate a surface of an intervertebal disc during surgery. Further, the ratchet arms 203, 205 of the docking anchor 201 are resiliently biased apart to engage serrations 200, 202 of the blade to secure the docking anchor 201 to the blade 12 at a desired position.

Figure 32:
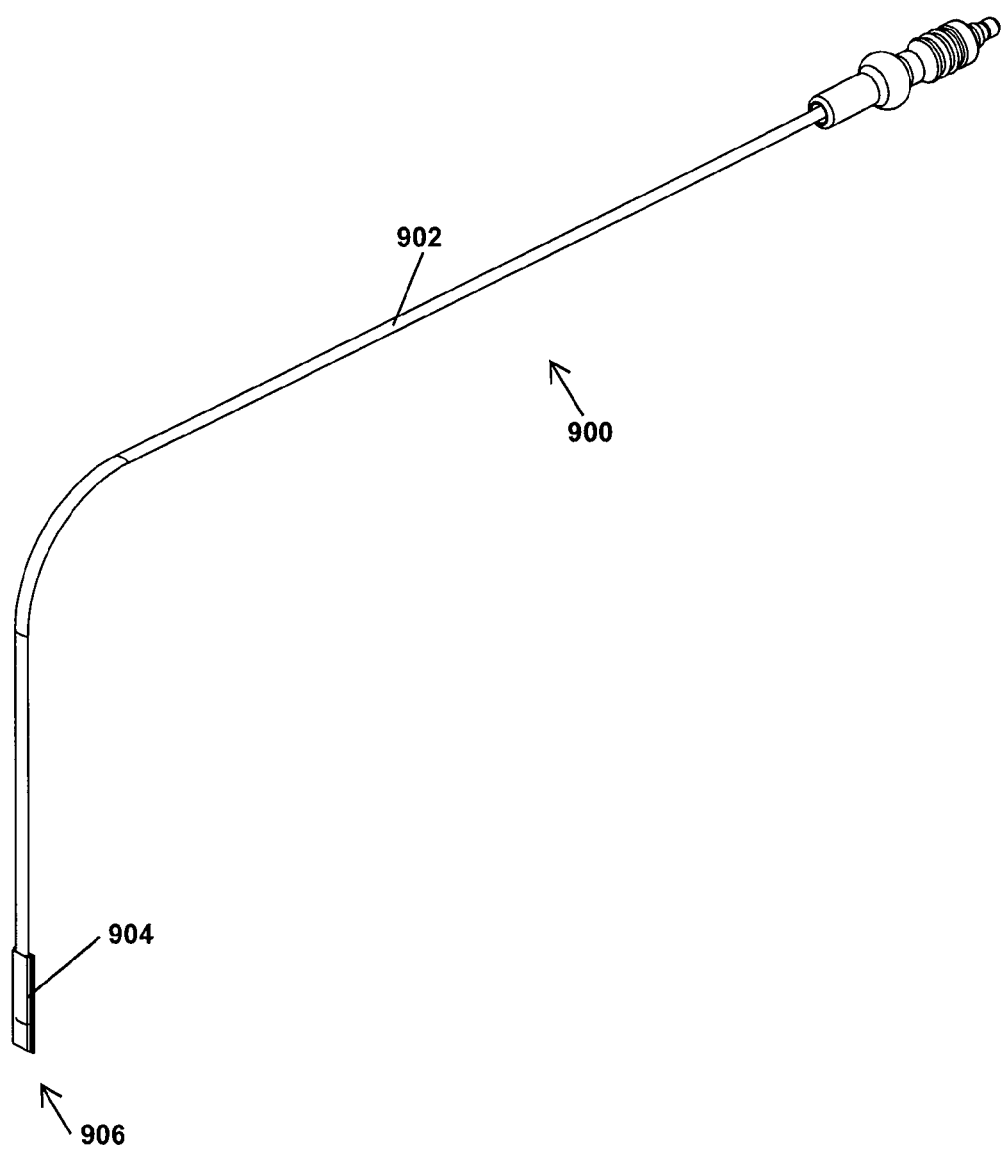
FIG. 32 is a perspective view of a light source showing a flexible fiber optic cable.

As shown in FIG. 32, a disposable light source 900 for use with the retractor 600 is shown. The disposable light source 900 has a flexible fiber optic cable 902 and an anodized aluminum tip 904 sized to fit within a slot of a retractor blade, such as the slot 190 of retractor blade 60 shown in FIG. 5. The tip 904 includes a light source 906 for illuminating a retracted incision, such as the working channel 640 shown in FIG. 22.

Figure 33:
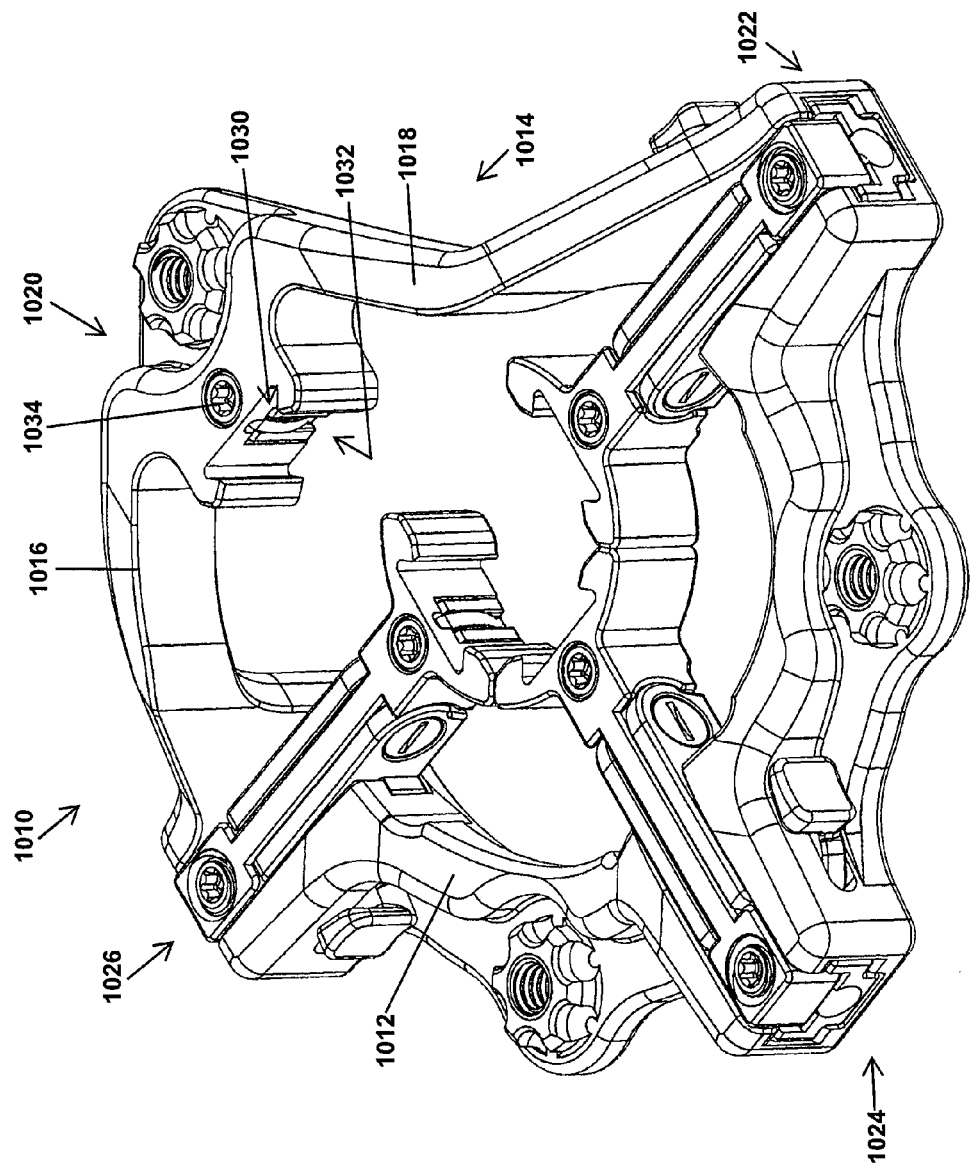
FIG. 33 is a perspective view of a retractor in accordance with another form of the present invention showing an elevated portion of the retractor frame.

With reference to FIG. 33, a retractor 1010 in accordance with another aspect of the present invention is illustrated. The retractor 1010 is substantially similar to the retractor 600 such that the differences therebetween will be highlighted. The retractor 1010 has a frame 1012 including a raised portion 1014 that accommodates placement of the retractor 1010 adjacent a patient's iliac crest. The raised portion 1014 includes a pair of arms 1016, 1018 supporting an operating mechanism 1020 disposed above the plane of the other operating mechanisms 1022, 1024, 1026. The operating mechanism 1020 has a dovetail recess 1030 and a wedge lock 1032 operable via a screw 1034 similar to operating mechanism 604 discussed above; however, the operating mechanism 1010 lacks a slider to retract the associated retractor blade.

Figure 34:
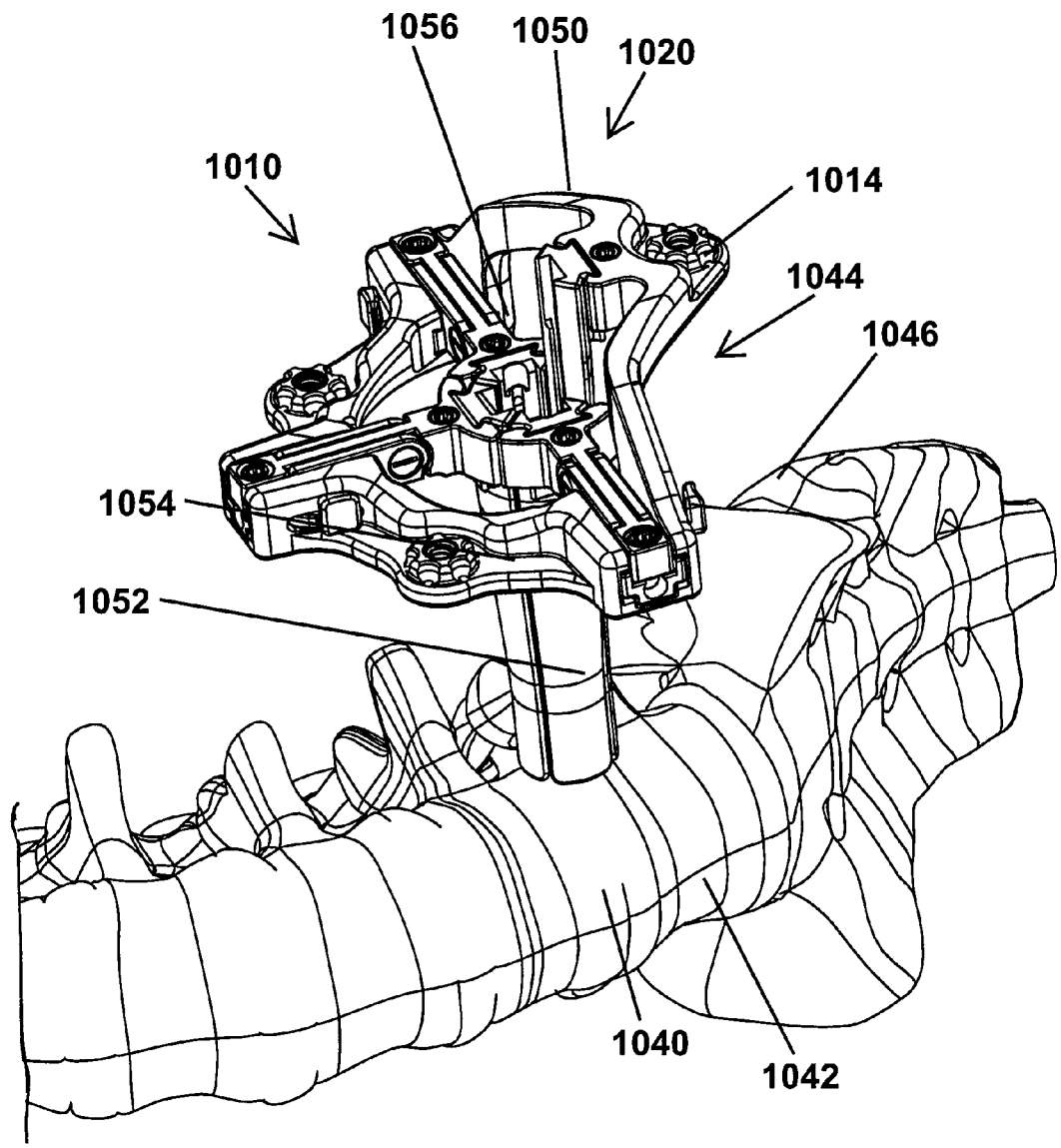
FIG. 34 is a perspective view of the retractor of FIG. 33 showing blades mounted on the retractor and disposed adjacent an intervertebral disc between L4 and L5 vertebrae.
Figure 35:
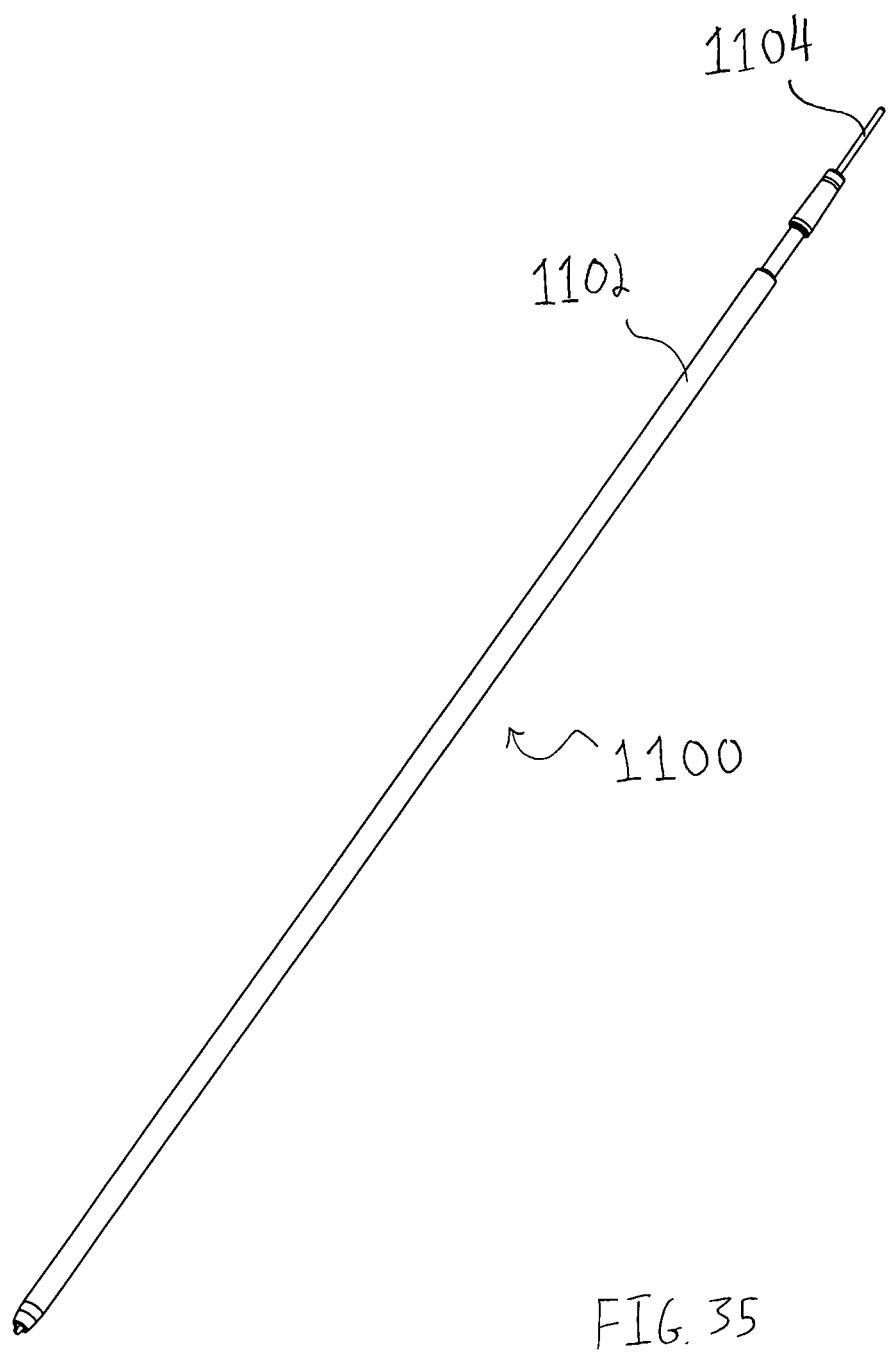
FIG. 35 is a perspective view of a pin dilator that may be used with the guide dilators of FIGS. 1, 7, and 8 in place of a separate guide wire and a first dilator.

As shown in FIG. 34, the retractor 1010 may be used to retract tissues adjacent lumbar vertebra 1040, 1042. The raised portion 1014 of the retractor 1010 provides spacing 1044 between the operating mechanism 1020 and an iliac crest 1046 of the patient. In this manner, a surgeon can position the raised portion 1014 upon a patient's hip while keeping the retractor 1010 relatively flush with the skin of the patient. The operating mechanism 1020 utilizes a longer blade 1050 to compensate for the distance the operating mechanism 1020 is elevated above the other operating mechanisms. Although blade 1050 is longer than the remaining blades 1052, 1054, 1056, the blades 1050, 1052, 1054, 1056 may all be inserted using a single guide dilator, such as guide dilator 10, in a manner substantially similar to the processes described above. The blade 1050 has a longer slot than the blades 1052, 1054, 1056 so that the distal ends of the blades 1050, 1052, 1054, 1056 will be disposed evenly at the leading end portion 46 of the guide dilator 10.

A pin dilator 1100 may also be used with the guide dilators 10, 300, 410 and surgical techniques described above. The pin dilator 1100 includes a dilator 1102 and a guide wire 1104 fixed in the dilator 1102. The pin dilator 1100 is an easy-tohandle tool that may be used in place of a conventional guidewire 514 and first dilator 516 (see FIG. 11).

Figure 36:
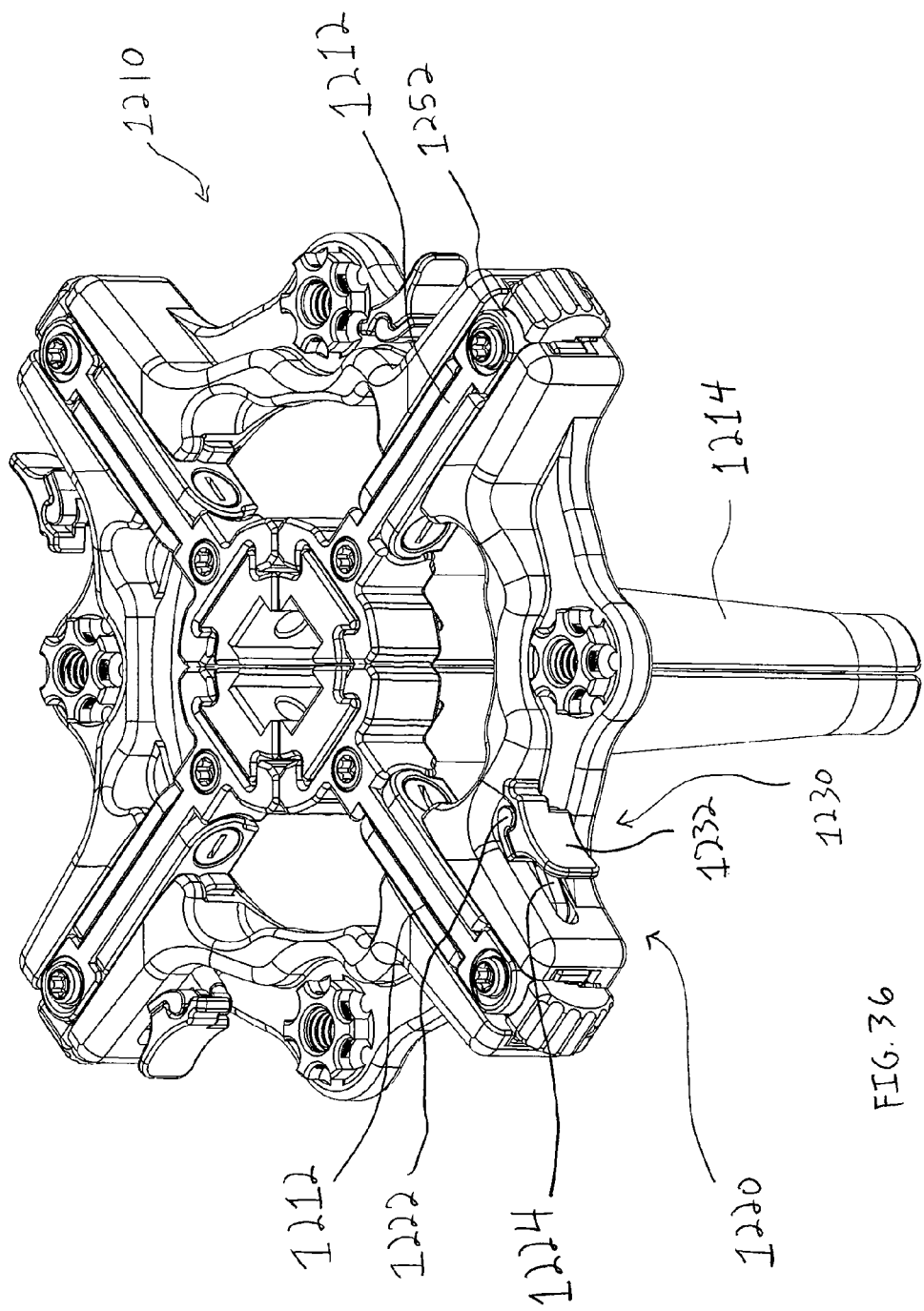
FIG. 36 is a perspective view of a retractor in accordance with another form of the present invention that includes locking mechanisms for locking sliders of the retractor.
Figure 37:
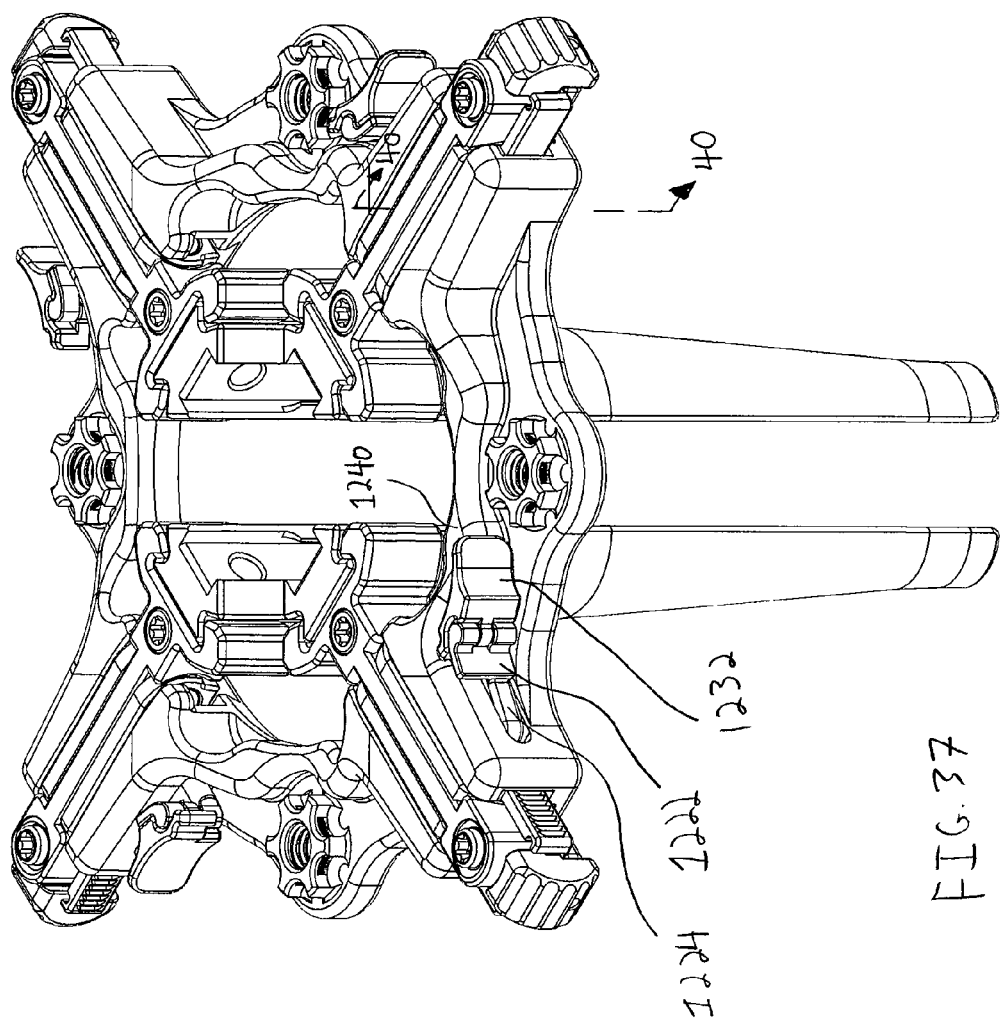
FIG. 37 is a perspective view of the retractor of FIG. 36 showing sliders and attached retractor blades of the retractor in a retracted configuration which generally forms a working channel between the blades.

Turning to FIGS. 36-41, a retractor 1210 in accordance with the present invention is shown. The retractor 1200 is similar in a number of ways to retractors 600 and 1010 and includes sliders 1212 connected to retractor blades 1214 which retract radially outward to enlarge an incision. The retractor 1200 includes a ratchet mechanism 1220 comprising a button 1222 and an integral tooth 1224 similar to the button 724 and tooth 717 (see FIG. 28) for selectively engaging the associated slider 1212, as shown in FIG. 36. The retractor 1200 further includes a slider lock mechanism 1230 comprising a lock latch 1232 that is pivotally connected to the button 1222. The slider lock mechanism 1230 fixes the tooth 1224 with the slider 1212 and reduces the chance that the ratchet mechanism 1220 may be accidentally disengaged during operation, which would permit the slider 1212 and associated retractor blade 1214 to shift radially inward. More specifically, when the slider 1212 as been retracted, a surgeon may pivot the lock latch 1232 toward a frame 1240 of the retractor 1200 such that the latch 1232 abuts the frame 1240 and restricts the button 1222 and integral tooth 1224 thereof from moving out of engagement with the slider 1212, as shown in FIG. 37.

Figure 38:
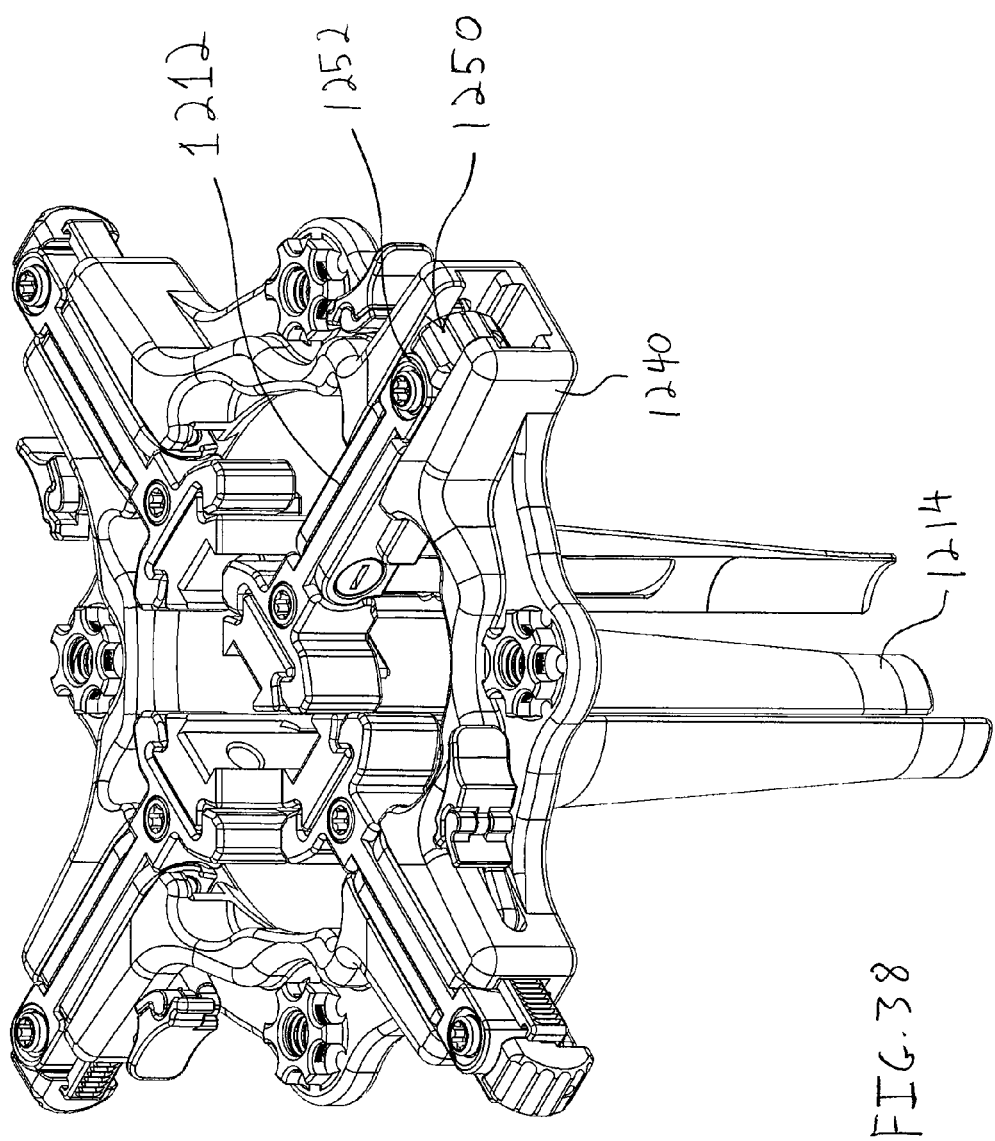
FIG. 38 is a perspective view of the retractor of FIG. 36 showing one of the sliders in a beyond center position where the retractor blade connected to the slider has been moved radially inward to a point beyond a center of the working channel.
Figure 39:
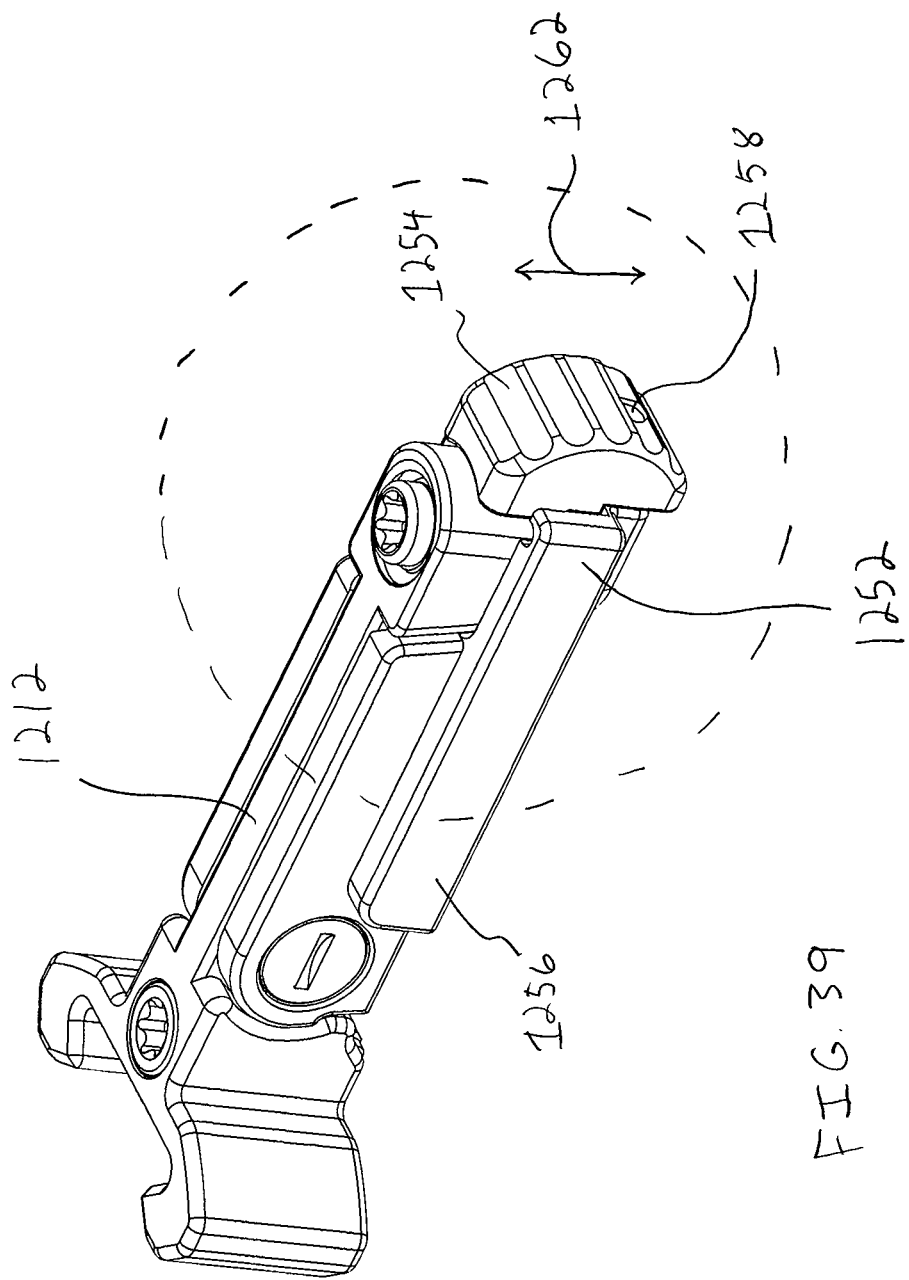
FIG. 39 is a perspective view of the slider shown in the beyond center position in FIG. 38 showing the slider removed from the retractor frame and a dashed circle extending about a locking mechanism of the slider.
Figure 40:
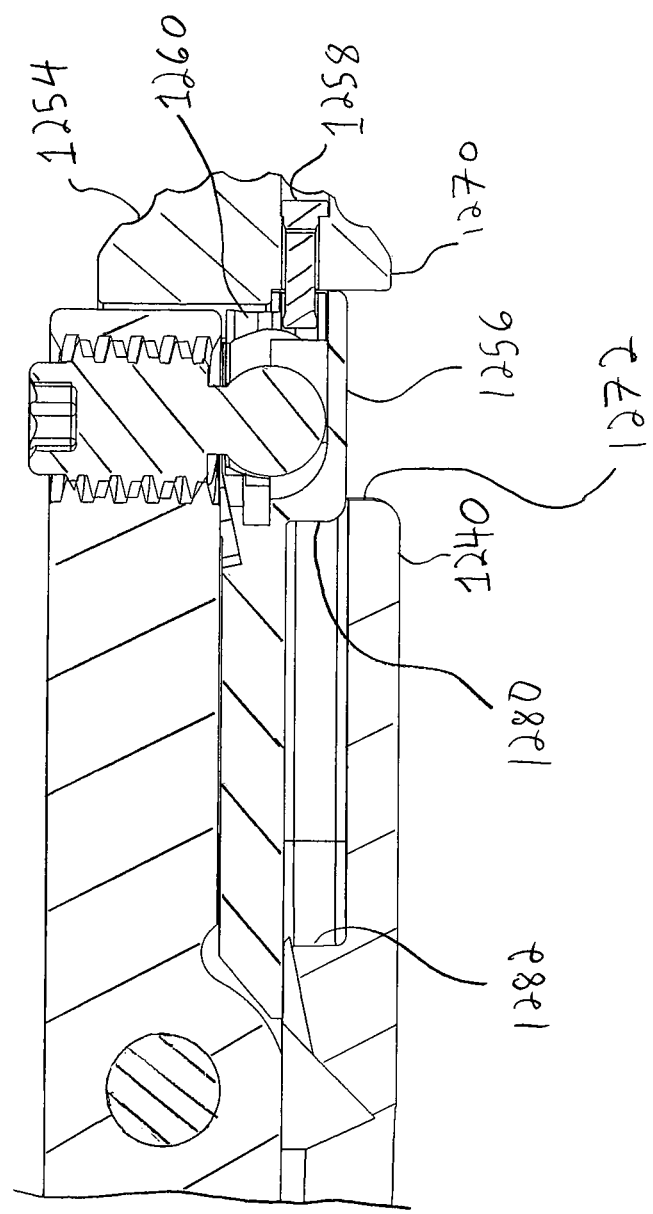
FIG. 40 is a cross sectional view taken across line 40-40 in FIG. 37 showing the slider in a retracted position and a lock button of the locking mechanism in a lowered locked position.

The retractor 1200 also permits a surgeon to move the sliders 1212 radially inward to a beyond center position where the associated retractor blade 1214 connected to the slider 1212 is beyond a center of a working channel defined by the retracted retractor blades 1214, as shown in FIG. 38. The retractor 1200 has a beyond center locking mechanism 1250 that controls whether a radially outer end 1252 of the slider 1212 may pass radially inward beyond the retractor frame 1240. The beyond center locking mechanism 1250 includes a lock button 1254 shiftably connected to a base 1256 of the slider 1212 by a pin 1258, as shown in FIGS. 39 and 40. The pin 1258 travels in a slot 1260 of the base 1256 and permits the lock button 1254 to shift up and down as shown by arrow 1262 in FIG. 39.

Figure 41:
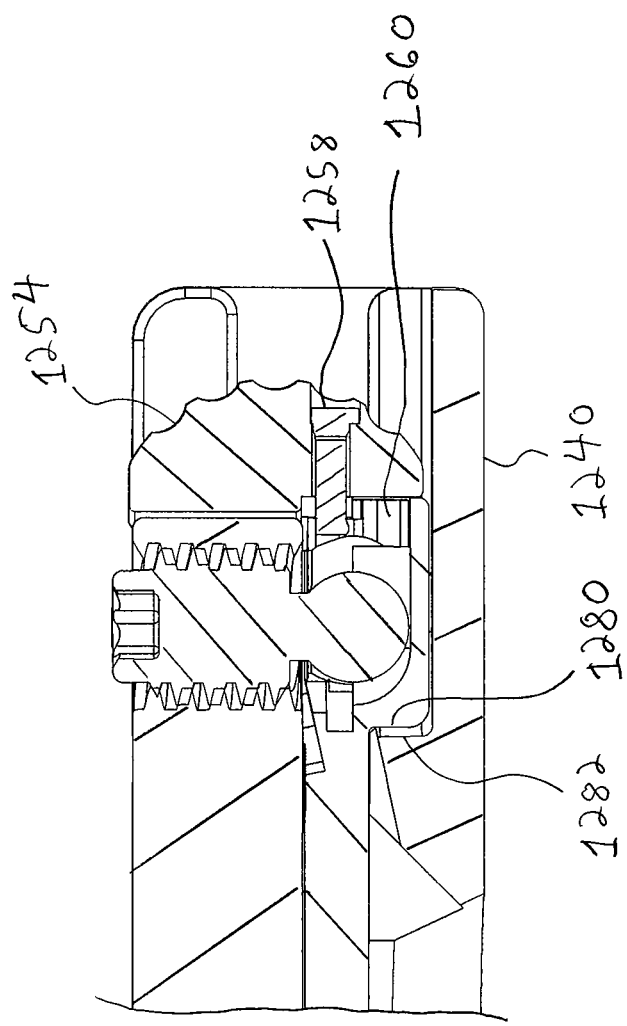
FIG. 41 is a cross sectional view similar to FIG. 40 showing the slider in the beyond center position and the lock button in a raised unlocked position.

For example, while retracting an incision, stray tissues may extend into the working channel between blades 1214. In prior approaches, a surgeon would need to insert a tool into the surgical field and tuck the stray tissues behind the nearby retractor blades 1214 to remove the stray tissues from the working channel. By contrast, a surgeon utilizing the retractor 1200 who encounters stray tissues in the working channel, may simply shift the button 1254 upward so that a lower end 1270 is in clearance with a radially outer wall 1272 of the retractor frame 1240, as shown in FIGS. 40 and 41. The surgeon then may move the slider 1212 and retractor blade 1214 radially inward to the beyond center position, as shown in FIG. 38. The slider 1212 and retractor frame 1240 include confronting surfaces 1280, 1282 that abut and limit movement of the slider 1212 radially inward to a predetermined position along the retractor frame 1240.

Those skilled in the art will recognize that a wide variety of modifications, alterations, and combinations can be made with respect to the above described embodiments without departing from the spirit and scope of the invention, and that such modifications, alterations, and combinations, are to be viewed as being within the scope of the invention.

What is claimed is:

1. A retractor for enlarging an incision, the retractor comprising:
   a frame extending about a central opening of the frame;
   a plurality of tissue engaging members for being inserted into an incision;
   a plurality of operating mechanisms for connecting the tissue engaging members to the frame and being operable to move the tissue engaging members apart to enlarge the incision;
   a slider of one of the operating mechanisms for being connected to one of the tissue engaging members, the slider being slidably connected to the frame and shiftable between extended and retracted positions; and
   a rotatable actuator of the slider operable to pivot the tissue engaging member relative to the frame and having a tool-receiving portion configured to receive a separate tool for rotating the actuator and causing the tissue engaging member to pivot relative to the frame,
   wherein the slider includes a pivotal support having a tissue engaging member portion for being connected to the tissue engaging member and an actuator portion connected to the rotatable actuator with the support being pivotal about a pivot axis intermediate the tissue engaging member portion and the actuator portion along the support.

2. The retractor of claim 1 wherein the operating mechanism includes a ratchet mechanism that permits the slider to shift toward the retracted position and resists movement of the slider toward the extended position.

3. The retractor of claim 1 wherein the pivot axis is closer to the tissue engaging member portion than the actuator portion along the support.

4. The retractor of claim 1 wherein the slider includes a slider body slidably connected to the frame and the support is pivotally connected to the slider body; and
   the operating mechanism includes a ratchet mechanism that includes a portion of the slider body, the ratchet mechanism permitting the slider to shift toward the retracted position and resists movement of the slider toward the extended position.

5. The retractor of claim 1 wherein the tool-receiving portion of the rotatable actuator includes an end portion of the rotatable actuator.

6. A retractor for enlarging an incision, the retractor comprising:
   a frame extending about a central opening of the frame;
   a plurality of tissue engaging members for being inserted into an incision;
   a plurality of operating mechanisms for connecting the tissue engaging members to the frame and being operable to move the tissue engaging members apart to enlarge the incision;
   a slider of one of the operating mechanisms for being connected to one of the tissue engaging members, the slider being slidably connected to the frame and shiftable between extended and retracted positions; and
   a rotatable actuator of the slider operable to pivot the tissue engaging member relative to the frame and having a tool-receiving portion configured to receive a separate tool for rotating the actuator and causing the tissue engaging member to pivot relative to the frame,
   wherein the slider includes a pivotal support for being connected to the tissue engaging member and a rotary connection between the rotatable actuator and the support configured so that the rotatable actuator applies force against the support in response to rotation of the actuator which pivots the support and the tissue engaging member connected thereto.

7. The retractor of claim 6 wherein the slider includes a slider body slidably connected to the frame and the support is pivotally connected to the slider body.

8. The retractor of claim 7 wherein the operating mechanism includes a ratchet mechanism comprising a tooth for being engaged with depressions of the slider body that permits the slider to shift toward the retracted position and resists movement of the slider toward the extended position.

9. The retractor of claim 6 wherein the tool-receiving portion of the rotatable actuator includes an end portion of the rotatable actuator and the rotary connection between the actuator and the support includes cooperating threads of the actuator and the support.

10. A retractor for enlarging an incision, the retractor comprising:
a frame extending about a central opening of the frame;
a plurality of tissue engaging members for being inserted into an incision;
a plurality of operating mechanisms for connecting the tissue engaging members to the frame and being operable to move the tissue engaging members apart to enlarge the incision;
a slider of one of the operating mechanisms for being connected to one of the tissue engaging members, the slider being slidably connected to the frame and shiftable between extended and retracted positions; and
a rotatable actuator of the slider operable to pivot the tissue engaging member relative to the frame and having a tool-receiving portion configured to receive a separate tool for rotating the actuator and causing the tissue engaging member to pivot relative to the frame,
wherein the slider includes a slider body slidably connected to the frame and a support for being connected to the tissue engaging member pivotally connected to the slider body with the rotatable actuator being connected to both the slider body and the support so that rotation of the actuator pivots the support and tissue engaging member connected thereto relative to the slider body.

11. The retractor of claim 10 wherein the connection between the actuator and the slider body includes a ball and socket that permits the actuator to pivot relative to the slider body with pivoting of the support and the tissue engaging member connected thereto.

12. The retractor of claim 10 wherein the slider body has a channel and the support includes a lever arm extending in the slider body channel with a portion of the lever arm shifting outward from the channel with pivoting of the support and tissue engaging member connected thereto.

13. The retractor of claim 10 wherein the tool-receiving portion of the rotatable actuator includes an end portion of the rotatable actuator.

14. A retractor for enlarging an incision, the retractor comprising:
a frame extending about a central opening of the frame;
a plurality of tissue engaging members for being inserted into an incision;
a plurality of operating mechanisms for connecting the tissue engaging members to the frame and being operable to move the tissue engaging members apart to enlarge the incision;
a slider of one of the operating mechanisms for being connected to one of the tissue engaging members, the slider being slidably connected to the frame and shiftable between extended and retracted positions; and
a rotatable actuator of the slider operable to pivot the tissue engaging member relative to the frame and having a tool-receiving portion configured to receive a separate tool for rotating the actuator and causing the tissue engaging member to pivot relative to the frame,
wherein the slider includes a locking mechanism reconfigurable between unlocked and locked configurations to secure the tissue engaging member to the slider with the locking mechanism including a wedge member and an inclined surface and reconfiguring the locking mechanism from the unlocked configuration to the locked configuration includes shifting the wedge member along the inclined surface and against the tissue engaging member.

15. The retractor of claim 14 wherein the locking mechanism includes a rotatable actuator connected to the wedge member so that rotation of the actuator shifts the wedge member along the inclined surface.

16. A retractor for enlarging an incision, the retractor comprising:
a frame extending about a central opening of the frame;
a plurality of tissue engaging members for being inserted into an incision;
a plurality of operating mechanisms for connecting the tissue engaging members to the frame and being operable to move the tissue engaging members apart to enlarge the incision;
a slider of one of the operating mechanisms for being connected to one of the tissue engaging members, the slider being slidably connected to the frame and shiftable between extended and retracted positions; and
a rotatable actuator of the slider operable to pivot the tissue engaging member relative to the frame and having a tool-receiving portion configured to receive a separate tool for rotating the actuator and causing the tissue engaging member to pivot relative to the frame,
wherein the slider includes a support pivotal about a pivot axis, the support having a tissue engaging member portion for being connected to the tissue engaging member and an arm portion extending from the tissue engaging member portion to the pivot axis with the arm portion having a predetermined length so that the tissue engaging member connected to the support travels along an arc about the pivot axis with pivoting of the support.

17. The retractor of claim 16 wherein the support includes an actuator portion connected to the rotatable actuator and a second arm portion extending from the actuator portion to the pivot axis and having a length that is longer than the length of the arm portion extending from the tissue engaging member portion to the pivot axis.

18. A retractor for enlarging an incision, the retractor comprising:
a frame extending about a central opening of the frame;
a plurality of tissue engaging members for being inserted into an incision;
a plurality of operating mechanisms for connecting the tissue engaging members to the frame and operable to move the tissue engaging members apart to enlarge the incision;
a slider of one of the operating mechanisms for being connected to one of the tissue engaging members, the slider being slidably connected to the frame and shiftable between an inward, extended position with the tissue engaging member in the central opening of the frame and an outward, retracted position with the tissue engaging member in the central opening of the frame;
a stop associated with the frame; and
a slider travel lock mechanism of the slider including a locking member shiftable from a locked position in which the locking member is positioned to abut the stop and restrict shifting of the slider inward beyond the extended position along the retractor frame and an unlocked position in which the locking member is in clearance with the stop to permit the slider to travel farther inward beyond the extended position.

19. The retractor of claim 18 wherein the stop includes an outer wall of the frame and the locking member is positioned to abut the frame outer wall with the locking member in the locked position thereof to restrict shifting of the slider inward beyond the extended position of the slider.

20. The retractor of claim 18 further comprising an inner stop associated with the frame and disposed inward from the stop; and an inner stop surface of the slider disposed along the slider inward from the locking member and configured to engage the inner stop and restrict inward shifting of the slider with the locking member in the unlocked position thereof.

21. The retractor of claim 18 wherein the slider includes a slider body slidably connected to the frame and a support pivotally connected to the slider body that receives the tissue engaging member; and the locking member is shiftably mounted on the support.

22. The retractor of claim 21 wherein the locking member and the support include a guide slot and a guide member extending into the guide slot such that shifting the locking member from the locked position to the unlocked position includes shifting one of the guide slot and the guide projection relative to the other of the guide slot and the guide projection.

23. The retractor of claim 22 wherein the locking member is a button and the guide projection is a pin extending into the guide slot.

\* \* \* \* \*